(12) United States Patent
Estes et al.

(10) Patent No.: US 11,357,998 B2
(45) Date of Patent: Jun. 14, 2022

(54) WEARABLE ULTRAVIOLET LIGHT PHOTOTHERAPY DEVICE

(71) Applicant: Sensor Electronic Technology, Inc., Columbia, SC (US)

(72) Inventors: Faris Mills Morrison Estes, West Columbia, SC (US); Robert M. Kennedy, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 16/142,955

(22) Filed: Sep. 26, 2018

(65) Prior Publication Data

US 2019/0099613 A1    Apr. 4, 2019

Related U.S. Application Data

(60) Provisional application No. 62/566,415, filed on Sep. 30, 2017.

(51) Int. Cl.
*A61N 5/06* (2006.01)
*A61L 2/10* (2006.01)
(Continued)

(52) U.S. Cl.
CPC .......... *A61N 5/0616* (2013.01); *A61B 5/0071* (2013.01); *A61L 2/10* (2013.01);
(Continued)

(58) Field of Classification Search
CPC ............ A61N 5/0616; A61N 2005/067; A61N 2005/0665; A61N 2005/0626;
(Continued)

(56) References Cited

U.S. PATENT DOCUMENTS 7,553,456 B2    6/2009    Gaska et al.
7,634,996 B2   12/2009    Gaska et al.
(Continued)

FOREIGN PATENT DOCUMENTS

JP    2017076553 A    5/2017
WO   2019067808 A2    4/2019

OTHER PUBLICATIONS

Han, I., Application No. PCT/US2018/053253, Search Report and Written Opinion, dated May 7, 2019, 14 pages.

*Primary Examiner* — Nathan J Jenness
(74) *Attorney, Agent, or Firm* — LaBatt, LLC

(57) ABSTRACT

A wearable ultraviolet light phototherapy device is disclosed. The wearable ultraviolet light phototherapy device can have a substrate or a housing that is to be worn on a body part of a patient. At least one ultraviolet light emitting source located about the substrate or housing can deliver ultraviolet radiation into the body part of the patient. A control module can control operation of the at least one ultraviolet light emitting source. To this extent, the control module can direct the at least one ultraviolet light emitting source to deliver a predetermined amount of ultraviolet radiation at a peak wavelength into the body part of a patient. The control module can determine the predetermined amount of ultraviolet radiation as a function of the patient's susceptibility to ultraviolet radiation.

20 Claims, 8 Drawing Sheets

(51) Int. Cl.
   *A61B 5/00* (2006.01)
   *A61B 5/01* (2006.01)
   *A61N 5/067* (2006.01)

(52) U.S. Cl.
   CPC .............. *A61B 5/0077* (2013.01); *A61B 5/01* (2013.01); *A61B 5/443* (2013.01); *A61N 5/067* (2021.08); *A61N 2005/0626* (2013.01); *A61N 2005/0645* (2013.01); *A61N 2005/0651* (2013.01); *A61N 2005/0654* (2013.01); *A61N 2005/0661* (2013.01); *A61N 2005/0662* (2013.01); *A61N 2005/0665* (2013.01)

(58) Field of Classification Search
   CPC .... A61N 2005/0645; A61N 2005/0662; A61B 5/0071; A61B 5/01; A61B 5/0077; A61B 5/443
   See application file for complete search history.

(56) References Cited

U.S. PATENT DOCUMENTS

| | | | |
|---|---|---|---|
| 8,277,734 B2 | 10/2012 | Koudymov et al. | |
| 8,980,178 B2 | 3/2015 | Gaska et al. | |
| 9,006,680 B2 | 4/2015 | Bettles et al. | |
| 9,034,271 B2 | 5/2015 | Shur et al. | |
| 9,061,082 B2 | 6/2015 | Gaska et al. | |
| 9,138,499 B2 | 9/2015 | Bettles et al. | |
| 9,179,703 B2 | 11/2015 | Shur et al. | |
| 9,572,903 B2 | 2/2017 | Dobrinsky et al. | |
| 9,603,960 B2 | 3/2017 | Dobrinsky et al. | |
| 9,687,577 B2 | 6/2017 | Dobrinsky et al. | |
| 9,707,307 B2 | 7/2017 | Shur et al. | |
| 9,718,706 B2 | 8/2017 | Smetona et al. | |
| 9,724,441 B2 | 8/2017 | Shur et al. | |
| 9,750,830 B2 | 9/2017 | Shur et al. | |
| 9,757,486 B2 | 9/2017 | Dobrinsky et al. | |
| 9,795,699 B2 | 10/2017 | Shur et al. | |
| 9,801,965 B2 | 10/2017 | Bettles et al. | |
| 9,802,840 B2 | 10/2017 | Shturm et al. | |
| 9,878,061 B2 | 1/2018 | Shur et al. | |
| 9,919,068 B2 | 3/2018 | Shur et al. | |
| 9,974,877 B2 | 5/2018 | Bettles et al. | |
| 9,981,051 B2 | 5/2018 | Shur et al. | |
| 9,987,383 B2 | 6/2018 | Bilenko et al. | |
| 9,999,782 B2 | 6/2018 | Shur et al. | |
| 10,099,944 B2 | 10/2018 | Smetona et al. | |
| 2002/0188218 A1* | 12/2002 | Lipman | A61N 5/0616 600/557 |
| 2007/0208395 A1 | 9/2007 | Leclerc et al. | |
| 2009/0080726 A1* | 3/2009 | Cotton | A61B 5/1075 382/128 |
| 2010/0179469 A1 | 7/2010 | Hammond et al. | |
| 2011/0191272 A1* | 8/2011 | McGuire | G01J 1/0219 706/11 |
| 2012/0330387 A1 | 12/2012 | Ferraz Rigo et al. | |
| 2013/0048545 A1 | 2/2013 | Shatalov et al. | |
| 2013/0172963 A1* | 7/2013 | Moffat | A61N 5/0613 607/94 |
| 2014/0074010 A1 | 3/2014 | Veres et al. | |
| 2014/0202962 A1 | 7/2014 | Bilenko et al. | |
| 2015/0032191 A1 | 1/2015 | Varghese et al. | |
| 2015/0297767 A1 | 10/2015 | Gaska et al. | |
| 2015/0336810 A1 | 11/2015 | Smetona et al. | |
| 2016/0074547 A1* | 3/2016 | Dobrinsky | A43B 17/10 250/492.1 |
| 2016/0114186 A1 | 4/2016 | Dobrinsky et al. | |
| 2016/0129279 A1 | 5/2016 | Ferolito | |
| 2017/0057842 A1 | 3/2017 | Dobrinsky et al. | |
| 2017/0100494 A1 | 4/2017 | Dobrinsky et al. | |
| 2017/0100495 A1 | 4/2017 | Shur et al. | |
| 2017/0189711 A1 | 7/2017 | Shur et al. | |
| 2017/0245527 A1 | 8/2017 | Dobrinsky et al. | |
| 2017/0245616 A1 | 8/2017 | Lakios et al. | |
| 2017/0281812 A1 | 10/2017 | Dobrinsky et al. | |
| 2017/0290934 A1 | 10/2017 | Dobrinsky et al. | |
| 2017/0368215 A1 | 12/2017 | Shatalov et al. | |
| 2018/0028700 A1 | 2/2018 | Dobrinsky et al. | |
| 2018/0092308 A1 | 4/2018 | Barber et al. | |
| 2018/0104368 A1 | 4/2018 | Dobrinsky et al. | |
| 2018/0117194 A1 | 5/2018 | Dobrinsky et al. | |
| 2018/0185529 A1 | 7/2018 | Shur et al. | |
| 2018/0221521 A1 | 8/2018 | Shur et al. | |
| 2018/0243458 A1 | 8/2018 | Shatalov et al. | |
| 2018/0321700 A1* | 11/2018 | Kwak | A61B 5/01 |
| 2018/0339075 A1 | 11/2018 | Kennedy et al. | |
| 2019/0030477 A1 | 1/2019 | Shatalov | |
| 2019/0100718 A1 | 4/2019 | Estes et al. | |

* cited by examiner

WEARABLE ULTRAVIOLET LIGHT PHOTOTHERAPY DEVICE

REFERENCE TO RELATED APPLICATIONS

The present patent application claims the benefit of U.S. Provisional Application No. 62/566,415, filed on 30 Sep. 2017, which is incorporated herein by reference in its entirety.

TECHNICAL FIELD

The disclosure relates generally to light therapy, and more particularly, to wearable ultraviolet light phototherapy devices that can increase vitamin D in a patient without over-exposing the patient to excessive amounts of ultraviolet radiation.

BACKGROUND ART

Vitamin D is produced by the body in response to skin being exposed to sunlight. It is also occurs naturally in a few foods including some fish, fish liver oils, egg yolks and in fortified dairy and grain products. Vitamin D is essential for strong bones, because it helps the body use calcium from the diet. Traditionally, Vitamin D deficiency has been associated with rickets, a disease in which the bone tissue doesn't properly mineralize, leading to soft bones and skeletal deformities. Increasingly, research is revealing the importance of vitamin D in protecting against a host of health problems.

Symptoms of bone pain and muscle weakness can correspond to a vitamin D deficiency. However, for many people, the symptoms of vitamin D deficiency are subtle. Yet, even without symptoms, too little vitamin D can pose health risks. Low blood levels of Vitamin D have been associated with a multiple of health problems that can include, but are not limited to, an increased risk of death from cardiovascular disease, cognitive impairment in older adults, severe asthma in children, and cancers.

Vitamin D deficiency can occur for a number of reasons. One reason is because a person's exposure to sunlight is limited. For example, living in northern latitudes, wearing long robes or head coverings, or having an occupation that prevents sun exposure are just a few reasons why a person may have limited exposure to sunlight. If a person's exposure to sunlight is limited, there is an increased risk of vitamin D deficiency because the body cannot make the vitamin when the skin is not exposed to sunlight. Other reasons why a vitamin D deficiency can occur include but are not limited to, a person has dark skin which reduces the skin's ability to make vitamin D in response to sunlight exposure, a person's kidneys cannot convert vitamin D to its active form, a person's digestive tract cannot adequately absorb vitamin D, and a person has a medical condition that affects the intestine's ability to absorb vitamin D from the food that is consumed, and a person is obese.

Treatment for vitamin D deficiency can involve getting more vitamin D through diet and supplements and/or increasing one's exposure to sunlight. However, both treatment options have their drawbacks. For example, vitamin D fortification through diet and supplements can lead to excessive amounts of vitamin D due to the difficulty in monitoring a person's vitamin D level and knowing what level of the vitamin is a safe amount for that person. Some studies suggest that excessive amounts of vitamin D can lead to increased mortality and incidence of vascular disease and other conditions. Although some exposure to sunlight has been found to be beneficial (e.g., moderating hypertension, high blood sugar and many other conditions), too much exposure to sunlight can increase one's risk to skin cancer and DNA mutations. Finding the right balance between insufficient exposure to sunlight and excessive exposure is very difficult as the best exposure for an individual will vary with skin characteristics. For example, the ratio between too much and too little exposure may be relatively small, such as less than a factor of roughly three for face and arm exposure or relatively large such as a factor of 25 for whole body exposure.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to wearable ultraviolet light phototherapy devices that increase vitamin D content (e.g., vitamin $D_3$) in a patient without over-exposing the patient to ultraviolet radiation. Further, the wearable ultraviolet light phototherapy devices can produce more vitamin $D_3$ in a patient in less time than if one spent the same amount of time exposed to sunlight. The wearable ultraviolet light phototherapy devices can also emit a much narrower band of UV-B light than what a patient would receive if one was exposed to sunlight, thereby decreasing the likelihood of skin damage that can occur when the skin is exposed to higher wavelengths of ultraviolet radiation. Additionally, the wearable ultraviolet light phototherapy devices can limit an area of the skin exposed to ultraviolet radiation to only a specific, desired area.

The wearable ultraviolet light phototherapy devices can take the form of any of a number of wearable articles that can be worn, held, placed, arranged, disposed, attached, etc., on a body part of a patient that has a need for phototherapy such as a human being or even an animal. Bracelets including ankle bracelets, bands (e.g., wrist bands, ankle bands), belts (e.g., arm belts), necklaces, earrings, watches, rings, are only a few non-exhaustive examples of possible wearable articles that can be configured as a wearable ultraviolet light phototherapy device that can incorporate the features of the various embodiments described herein. In this manner, the wearable ultraviolet light phototherapy devices can be placed on skin areas that experience less exposure to sunlight such as the upper legs, arms, abdomen and back, thus minimizing the risk for developing non-melanoma skin cancer. In a different type of use, the wearable ultraviolet light phototherapy devices can be configured for other applications beyond phototherapy. For example, in an unworn state (e.g., removed from the body part of the patient), the devices can be used as hand-held disinfection devices to disinfect the surfaces of a number of different objects, items, and the like.

Each of the various embodiments described herein can utilize at least one ultraviolet light emitting source to irradiate the skin of a patient. An ultraviolet light emitting diode (UV LED) is one type of ultraviolet light emitting source that can be used for the irradiation of a patient's skin in order to effectuate a phototherapy treatment. In particular, the UV LED can operate at a wavelength that ranges from about 295 nanometers (nm) to about 315 nm in order to expose the patient's skin to ultraviolet radiation in the UV-B range. In one embodiment, a set of ultraviolet light emitting sources such as UV LEDs can be utilized, with at least one of the sources configured to operate at a wavelength that ranges from about 295 nm to about 315 nm. Another of the sources can be configured to operate at a wavelength that ranges from about 100 nm to 280 nm to generate ultraviolet radiation in the UV-C range for scenarios in which the wearable ultraviolet light therapy device is used for disinfection purposes.

The ultraviolet light emitting source(s) can be placed in a substrate or a housing that can be worn by the patient. For example, the substrate and the housing can be worn on a particular body part of a patient. In one embodiment, the substrate and the housing can conform to the patient's body part. To this extent, the substrate and the housing can include a semi-flexible or flexible medium or material that receives, slides over or wraps around the body part. In another embodiment, the substrate and the housing can adhere to or be applied to a portion of skin of the patient. The substrate or a housing can include one or more optical elements that facilitate the transmission of the ultraviolet radiation to the skin of the patient. Examples of optical elements that can be incorporated with the substrate or the housing can include, but are not limited to, reflecting elements (e.g., mirrors, pyramid-shaped reflector), light prisms and lenses.

In one embodiment, the substrate and the housing can include a multi-layered structure. For example, the substrate and the housing can have a reflective outer layer, a diffusive layer, and a core layer positioned between the reflective outer layer and the diffusive layer. In one embodiment, the core layer can be coupled to the ultraviolet light emitting source(s). In this manner, the reflective outer layer can reflect the ultraviolet radiation generated from the ultraviolet light emitting source(s) towards the diffusive layer which diffuses the radiation into the body part of the patient. In one embodiment, the reflective outer layer can include an ultraviolet reflective material that enables recycling of the ultraviolet radiation generated from the ultraviolet light emitting source(s). Examples of ultraviolet reflective material can include polished aluminum, PTFE, expanding polytetrafluoroethylene (ePTFE), ETFE or combinations thereof. In another embodiment, the ultraviolet reflective layer can include a diffusive ultraviolet reflective layer such as a coating or thin film of a fluoropolymer (e.g., ePTFE, PTFE, and/or the like). In one embodiment, the core layer can include an ultraviolet transparent layer. The ultraviolet transparent layer can include a transparent fluoropolymer material. Examples of a transparent fluoropolymer material can include, but is not limited to, EFEP, FEP, PTFE, ECTFE, PCTFE, PFA, PVDF, ETFE, THV, LDPE and MFA.

The ultraviolet transparent layer can also include an ultraviolet transparent fluid such as distilled water, purified water, potable water, and a transparent gas. In one embodiment, the core layer can define a void formed between the reflective outer layer and the diffusive layer. In one embodiment, the core layer can include a light guiding layer or media. In one embodiment, the diffusive layer can include an ultraviolet transparent diffusive layer. Examples of an ultraviolet transparent diffusive layer include, but are not limited to, $SiO_2$, $Al_2O_3$, $CaF_2$, $MgF_2$, and/or the like. In one embodiment, the diffusive layer can include a layered arrangement of fluoropolymer films, voids, and/or light diffusing elements. In one embodiment, the diffusive layer can include a plurality of ultraviolet transparent protrusions configured to extract the ultraviolet radiation from the core layer into the body part of the patient.

The wearable ultraviolet light phototherapy devices of the various embodiments can further include a control module coupled to the ultraviolet light emitting source(s) to control the operation thereof. For example, the control module can direct the ultraviolet light emitting source(s) to deliver a predetermined amount of ultraviolet radiation into the body part of a patient at a peak wavelength in the aforementioned UV-B range. The control module can determine the predetermined amount of ultraviolet radiation as a function of the patient's susceptibility to ultraviolet radiation. Determining the patient's susceptibility to ultraviolet radiation depends on various factors that can include, but are not limited to, the patient's skin pigmentation and skin thickness, as well as a plurality of general patient parameters (e.g., the patient's skin dryness, skin temperature, age, weight, gender, race and existing medical conditions/history).

An input component can be coupled to the control module that permits entry of information relating to any of the aforementioned factors. For example, users of the wearable ultraviolet light phototherapy devices of the various embodiments can enter information that pertains to the general patient parameters. In addition, the input component can be used in other capacities. For example, a user can utilize the input component to manually adjust the predetermined amount of ultraviolet radiation delivered by the ultraviolet light emitting source to another amount. This can include changing one or more of the following settings: a dosage setting of the ultraviolet radiation delivered by the ultraviolet light emitting source(s), an intensity setting of the ultraviolet radiation of the ultraviolet light emitting source(s), a spatial coverage setting of the ultraviolet radiation applied to the body part of the patient by the ultraviolet light emitting source(s), a spectral power distribution setting of the ultraviolet light emitting source(s), and a duration setting that the ultraviolet radiation is applied to the body part of the patient by the ultraviolet light emitting source(s). In one embodiment, the input component can permit a user to activate and inactivate operation of the ultraviolet light emitting source(s) and/or any other types of light emitting sources (e.g., visible light emitting sources). In this manner, the patient can select an operating mode from one of a variety of different modes that are each configured to enable a specific amount and pattern of radiation to be directed to the patient's skin. For example, the input component can be utilized by a user to direct the ultraviolet light emitting source(s) to deliver the predetermined amount of ultraviolet radiation to the patient's skin in a pulsed mode of operation.

Other mechanisms can be used with the control module that facilitate obtaining information that relates to any of the above-noted factors. In one embodiment, an infrared camera can be utilized to obtain an infrared image of the patient's skin about a body part of the patient. The control module can then infer the skin temperature about the body part of the patient from the infrared image. In one embodiment, a visible camera can be configured to obtain an image of the patient's skin. The visible camera can then send the image to the control module for ascertaining the pigmentation and skin thickness about the body part of the patient. The visible camera can also be used to obtain an image of the patient's skin during and/or after receiving the predetermined amount of ultraviolet radiation from the ultraviolet light emitting source(s). The control module can ascertain changes in the skin color of the body part of the patient during and/or after receiving the predetermined amount of ultraviolet radiation. In this manner, the control module can monitor the irradiation of the patient and/or use the changes in skin color to determine how much ultraviolet radiation a patient should receive in subsequent treatments. In one embodiment, at least one visible light emitting source can be utilized to deliver visible light radiation into the body part of the patient. The at least one visible light emitting source can operate independently or in conjunction with the ultraviolet light emitting source(s).

At least one sensor can be operatively coupled to the ultraviolet light emitting source(s) and the control module, as well as any of the other mechanisms, in order to obtain operational data relating to the irradiation of the body part of the patient. The control module can control the operation of the source(s) and the visible camera as a function of the operational data. A number of sensors are well suited for use with any of the wearable ultraviolet light phototherapy devices described herein. For example, an ambient radiation sensor can be configured to obtain radiation conditions of an ambient environment surrounding the substrate or the housing. This allows the control module to determine whether there is a need to irradiate the body part of the patient with ultraviolet radiation depending on the obtained radiation conditions. In one embodiment, a fluorescent sensor can be utilized to detect fluorescence emitted from the body part of the patient after irradiation by the ultraviolet light emitting source(s). The control module can then determine changes in the patient's skin based on the detected fluorescence emitted from the body part.

In additional embodiments, other sensors that can be deployed to operate in conjunctions with the control module and the various sources include, but are not limited to, a temperature sensor, a pressure sensor, a heart rate sensor, a blood oxygen saturation level sensor, etc. In addition to making any of the aforementioned assessments, the control module can use the sensor(s) to monitor the irradiation of the body part of the patient with the ultraviolet light emitting source(s) and/or the visible light sources. In this manner, the control module can adjust the predetermined amount of ultraviolet radiation directed to the body part as function of the operational data obtained by the sensor(s).

A multiple of other components can be used to facilitate a phototherapy treatment of a patient with any of the ultraviolet light phototherapy devices described herein. For example, a timer can be utilized to ensure that the ultraviolet light emitting source(s) and visible light source(s) deliver a sufficient dosage of radiation to obtain a desired effect over a specified illumination time. In one embodiment, an output component that can include, but is not limited to, a visual display can provide status information on the operation of the wearable ultraviolet light phototherapy device and/or the treatment of the patient. For example, the output component can indicate status information of the treatment (e.g., on, off, treated, needs treatment, etc.), as well as generate information on more specific details of the treatment. A power supply component can power the ultraviolet light emitting source(s), the visible light emitting source(s), the control module, the sensors, the input component, the output component and the timer. The power supply component can include one of a number of different power sources. In one embodiment, the power supply component can include a rechargeable battery that can be recharged from an external port. For example, a USB, mini USB or other appropriate port can be used to charge the battery.

A first aspect of the invention provides a wearable ultraviolet light phototherapy device, comprising: a substrate configured to be worn on a body part of a patient; at least one ultraviolet light emitting source located about the substrate to deliver ultraviolet radiation into the body part of the patient via the substrate, wherein the at least one ultraviolet light emitting source emits ultraviolet-B (UV-B) radiation having a peak wavelength ranging from 295 nm to 315 nm; and a control module coupled to the at least one ultraviolet light emitting source to control the operation thereof, wherein the control module directs the at least one ultraviolet light emitting source to deliver a predetermined amount of ultraviolet radiation at the peak wavelength into the body part of a patient, the control module determining the predetermined amount of ultraviolet radiation as a function of the patient's susceptibility to ultraviolet radiation.

A second aspect of the invention provides a wearable ultraviolet light phototherapy device, comprising: a housing configured to be worn about a body part of a patient, the housing including an inner wall surface and an outer wall surface, wherein the inner wall surface adheres to a portion of skin of the patient and the outer wall surface faces an ambient environment external to the housing; an input component on the outer wall surface of the housing for receiving information relating to a plurality of general patient parameters; a set of ultraviolet light emitting sources placed in the housing to direct ultraviolet radiation toward the inner wall surface of the housing for transmission towards the portion of skin of the patient, wherein at least one of the ultraviolet light emitting sources operates with a peak wavelength ranging from 295 nm to 315 nm; at least one sensor to obtain operational data relating to the irradiation of the portion of skin of the patient; and a control module operatively coupled to the input component, the set of ultraviolet light emitting sources and the least one sensor to control the irradiation of the portion of skin of the patient, wherein the control module determines an amount of ultraviolet radiation to be directed towards the portion of skin of the patient based on the general patient parameters received by the input component and the operational data obtained by the at least one sensor, the control module specifying a plurality of irradiation parameters that enable the set of ultraviolet light emitting sources to deliver the determined amount of ultraviolet radiation towards the portion of skin of the patient, the control module and the at least one sensor monitoring the irradiation of the portion of skin of the patient, and the control module adjusting one or more of the plurality of irradiation parameters based on feedback provided by the at least one sensor.

A third aspect of the invention provides a wearable ultraviolet light phototherapy system, comprising: a housing configured to be worn about a body part of a patient, the housing including an inner wall surface and an outer wall surface, wherein the inner wall surface adheres to a portion of skin of the patient and the outer wall surface faces an ambient environment external to the housing; an input component on the outer wall surface of the housing for receiving information relating to a plurality of general patient parameters; a visible camera placed in the housing to obtain an image of the patient's skin about the body part of the patient; a set of ultraviolet light emitting sources placed in the housing to direct ultraviolet radiation toward the inner wall surface of the housing for transmission towards the portion of skin of the patient, wherein at least one of the ultraviolet light emitting sources operates with a peak wavelength ranging from 295 nm to 315 nm; at least one sensor to obtain operational data relating to the irradiation of the portion of skin of the patient; and a control module operatively coupled to the input component, the visible camera, the set of ultraviolet light emitting sources and the least one sensor to control the irradiation of the portion of skin of the patient, wherein the control module determines an amount of ultraviolet radiation to be directed towards the portion of skin of the patient based on the general patient parameters received by the input component, the image from the visible camera, and the operational data obtained by the at least one sensor, the control module specifying a plurality of irradiation parameters that enable the set of ultraviolet light emitting sources to deliver the determined amount of ultraviolet radiation towards the portion of skin of the patient, the control module, the at least one sensor and the visible camera monitoring the irradiation of the portion of skin of the patient, and the control module adjusting one or more of the plurality of irradiation parameters based on feedback provided by the at least one sensor and the visible camera.

BRIEF DESCRIPTION OF THE DRAWINGS

These and other features of the disclosure will be more readily understood from the following detailed description of the various aspects of the present invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
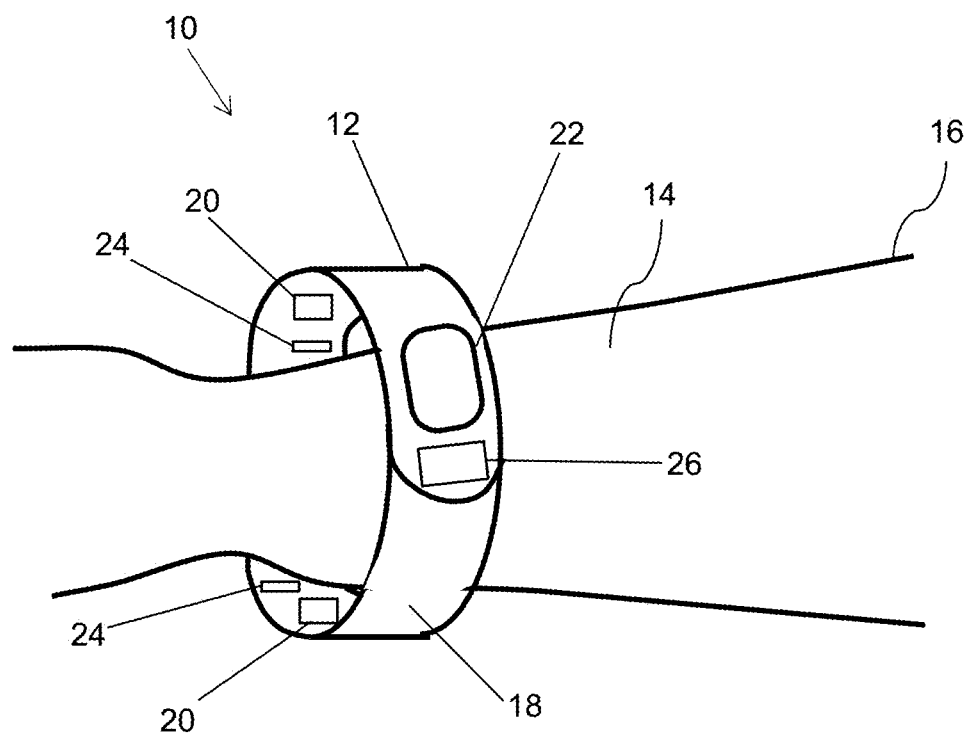
FIG. 1 shows a schematic of a wearable ultraviolet light phototherapy device in the form of a band according to an embodiment of the present invention.

As indicated above, aspects of the present invention are directed to wearable ultraviolet light phototherapy devices that increase vitamin D content (e.g., vitamin $D_3$) in a patient without over-exposing the patient to ultraviolet radiation. The wearable ultraviolet light phototherapy devices of the various embodiments can produce a greater amount of vitamin $D_3$ in a patient in less time than if one spent the same amount of time exposed to sunlight. The wearable ultraviolet light phototherapy devices can also emit a much narrower band of UV-B light than what a patient would receive if one was exposed to sunlight, thereby decreasing likelihood of skin damage that can occur when the skin is exposed to higher wavelengths of ultraviolet radiation. Additionally, the wearable ultraviolet light phototherapy devices can limit an area of the skin exposed to ultraviolet radiation to only a specific, desired area.

As used herein, a wearable ultraviolet light phototherapy device is an article that can be worn, held, placed, arranged, disposed, attached, on a body part of a patient and to deliver ultraviolet radiation to the body part as part of a phototherapy treatment. A wearable ultraviolet light phototherapy device further includes an article that can be held, grasped, or gripped by the body part of the patient in order to deliver ultraviolet radiation to the body part as part of a phototherapy treatment. The wearable ultraviolet light phototherapy devices of the various embodiments can take the form of any of a number of wearable articles. For example, the wearable ultraviolet light phototherapy devices can take the form of bracelets including ankle bracelets, bands (e.g., wrist bands, ankle bands), belts (e.g., arm belts), necklaces, earrings, watches, and rings. These are only a few examples of possible wearable articles that can be configured as a wearable ultraviolet light phototherapy device that can incorporate the below-mentioned components and functions, and are not meant to limit the applicability of the various embodiments to other types of articles. For example, other types of articles that conform to the above definition and that can incorporate the components and functions of the various embodiments include, but are not limited to, a hand-held pointing device (e.g., a computer mouse) and mobile phones (e.g., a cell phone, smart phone, etc.) and accompanying accessories (e.g., covers).

As used herein, phototherapy treatment means delivering ultraviolet radiation to a patient at a specific dosage, intensity, wavelength, type (e.g., UV-B), and the like, in order to improve or remedy a particular medical condition of the patient, improve general health and well-being of the patient, and/or the like. Examples of medical conditions that can benefit from a phototherapy treatment can include, but are not limited to, vitamin D deficiency, psoriasis, depression, eczema, and jaundice. Although the various embodiments are described with respect to human patients, it is understood that the wearable ultraviolet light phototherapy devices described herein can be used with other patients such as animals.

In other aspects, the wearable ultraviolet light phototherapy devices can be used to facilitate a cleaning treatment of surfaces of a number of different objects, items, and the like, while in an unworn state. As used herein, an unworn state of a wearable ultraviolet light phototherapy device means that the device has been removed from, taken off, unsecured from, etc., a body part of a patient. As used herein, a cleaning treatment can entail disinfecting, sterilizing, and/or sanitizing a surface of an object. Cleaning generally means the removal of visible soil (e.g., organic and inorganic material) from objects and surfaces. Disinfecting generally means destroying pathogenic and other types of microorganisms, while sterilizing is more extensive in that it kills all microbial forms. Sanitizing generally means reducing the number of bacterial contaminants to a predetermined safe level. As used herein, an object can include any item or article that varies in shape and size (e.g., phones, keypads, door knobs) with surfaces that are subject to human contact.

Although the various embodiments of the present invention described herein are directed to wearable ultraviolet light phototherapy devices that can facilitate a phototherapy treatment and a cleaning treatment in an unworn state, it is understood that these aspects are only a couple of examples of applications of use of the devices, and are not meant to limit the scope of the present invention. Furthermore, those skilled in the art will appreciate that the wearable ultraviolet light phototherapy devices described herein can include any now known or later developed approach that incorporates the concepts of the various embodiments of the present invention. The various wearable ultraviolet light phototherapy devices described herein can include a number of components (some of which may be optional). These components and the functions that each can perform are described below in more detail. The components can include any now known or later developed approaches that can facilitate implementation of the concepts and configurations of the various embodiments described herein.

Ultraviolet radiation, which can be used interchangeably with ultraviolet light, means electromagnetic radiation having a wavelength ranging from approximately 10 nanometers (nm) to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through.

The description that follows may use other terminology herein for the purpose of only describing particular embodiments and is not intended to be limiting of the disclosure. For example, unless otherwise noted, the term "set" means one or more (i.e., at least one) and the phrase "any solution" means any now known or later developed solution. The singular forms "a," "an," and "the" include the plural forms as well, unless the context clearly indicates otherwise. It is further understood that the terms "comprises," "comprising," "includes," "including," "has," "have," and "having" when used in this specification, specify the presence of stated features, integers, steps, operations, elements, and/or components, but do not preclude the presence or addition of one or more other features, integers, steps, operations, elements, components, and/or groups thereof.

Turning to the drawings, FIG. 1 shows a schematic of a wearable ultraviolet light phototherapy device 10 in the form of a band 12 according to an embodiment of the present invention. As shown in FIG. 1, the band 12 can include a wristband worn on the lower arm or wrist 14 of a person or patient 16 that is to undergo a phototherapy treatment. Although the embodiment depicted in FIG. 1 is described as a wristband, it is understood that other types of bands such as bracelets including metal bracelets, watches, and the like, are equally suitable for use as a wearable ultraviolet light phototherapy device that is worn about the wrist 14 of the patient 16.

In one embodiment, the wearable ultraviolet light phototherapy device 10 can include a substrate 18 that is configured to be worn on the wrist 14 of the patient 16. The substrate 18 is flexible in that it can bend, flex and conform to the shape and size of the wrist 14 of the patient 16 so that the substrate can be worn over the wrist. In this manner, the substrate 18 can tightly adhere to the person's body. The substrate 18 can be formed from a material that includes, but is not limited to, an elastomer material, a woven fabric, an elastic material, a metal or metal mesh, a plastic, and/or the like. In an embodiment, some or all of the substrate 18 can be formed of a flexible substrate as shown and described in U.S. Provisional Application No. 62/072,724, which was filed on 30 Oct. 2014, and which is hereby incorporated by reference.

In one embodiment, portions or the entire substrate 18 can include any ultraviolet transparent material such as an ultraviolet transparent fluoropolymer or waveguides formed from such a polymer. Examples of an ultraviolet transparent fluoropolymer that are suitable for use with the substrate 18 can include, but are not limited to, fluorinated ethylene-propylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), ethylene chlorotrifluoroethylene (ECTFE), polychlorotrifluoroethene (PCTFE), a copolymer of tetrafluoroethylene and perfluoro methyl alkoxy (MFA), low density polyethylene (LDPE), perfluoroether (PFA), and/or the like. Other examples of material that can be used in the substrate 18 to waveguide, transmit and diffuse ultraviolet radiation can also include fused silica, sapphire, quartz, anodized aluminum oxide (AAO), polylactide (PLA), and fluoride based materials such as calcium fluoride ($CaF_2$) or magnesium fluoride ($MgF_2$), and/or the like.

At least one ultraviolet light emitting source 20 can be located about the substrate 18 to deliver ultraviolet radiation into the skin near the wrist 14 of the patient 16 via the substrate 18. As used herein, having the ultraviolet light emitting source 20 located about the substrate means that the ultraviolet light emitting source 20 can be located on an inner wall surface, an internal portion and/or an outer wall surface of the substrate 18. In one embodiment, the ultraviolet light emitting source 20 can be monolithically embedded into the substrate 18 either through an opening on the outer wall surface of the substrate 18 or through attachment to the outer wall surface. In one embodiment, the ultraviolet light emitting source 20 can be removably coupled to and from the substrate, making it easier to replace the source as needed or exchanged with another a source.

In either configuration, ultraviolet radiation emitted from the ultraviolet light emitting source 20 can be transmitted into the substrate via an ultraviolet transparent window. In one embodiment, the ultraviolet light emitting source 20 can be incorporated within an internal portion of the substrate 18. In all of the possible arrangements, ultraviolet radiation can propagate through the substrate 18 for transmission into the skin of the patient 16 at the wrist 14.

The ultraviolet light emitting source 20 can comprise any combination of one or more ultraviolet radiation emitters to form a part of the ultraviolet light phototherapy device 10. Although FIG. 1 shows two ultraviolet light emitting sources 20, it is understood that the number of sources in this figure is illustrative of one arrangement and is not meant to be limiting as more or less ultraviolet light emitting sources 20 are possible. Examples of ultraviolet radiation emitters can include, but are not limited to, high intensity ultraviolet lamps (e.g., high intensity mercury lamps), discharge lamps, ultraviolet light emitting diodes (LEDs), super luminescent LEDs, laser diodes, and/or the like. In one embodiment, the ultraviolet light emitting source 20 can include a set of LEDs manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof).

The ultraviolet light emitting source 20 can be configured to delivered a variety of forms of ultraviolet radiation to the skin of the patient 16 near the wrist 14 at different bands of wavelengths. For example, the ultraviolet light emitting source 20 can emit UV-A radiation and/or UV-B radiation towards the wrist 14. In general, UV-A radiation and UV-B radiation can be used in a phototherapy treatment to treat a number of medical conditions such as vitamin D deficiency, psoriasis, eczema, jaundice and depression. It is understood that the type of radiation emitted from the ultraviolet light emitting source 20 into the body part of the patient 16 as well as the wavelength range of the radiation, will depend on the particular medical condition that the phototherapy treatment is being used to address. In one embodiment, the ultraviolet light emitting source 20 can deliver UV-B radiation to the wrist 14 of the patient 16 at a peak wavelength that ranges from 295 nm to 315 nm. Emitting UV-B radiation at a peak wavelength that ranges from 295 nm to 315 nm is advantageous in that efficacy is high for Vitamin D production, reducing the required intensity.

It is understood that the wrist 14 of the patient 16 can be irradiated according to other approaches and that having the ultraviolet light emitting source 20 emit only UV-B radiation at a peak wavelength that ranges from 295 nm to 315 nm is not meant to be exhaustive of all of the possible options. For example, in one embodiment, a first ultraviolet light emitting source 20 can emit UV-A radiation at a peak wavelength that ranges from 315 nm to 335 nm and a second ultraviolet light emitting source 20 can emit UV-B radiation at a peak wavelength that ranges from 295 nm to 315 nm to treat a patient having psoriasis. In one embodiment, one or more ultraviolet light emitting sources 20 can be configured to deliver UV-B radiation to a body part of the patient 16 in a pulsed-mode of operation in order to have the patient receive larger ultraviolet intensities without having overheating of the source(s).

A control module 22 can control the operation of the at least one ultraviolet light emitting source 20. For example, the control module 22 can direct the ultraviolet light emitting source 20 to deliver a predetermined amount of ultraviolet radiation at a peak wavelength into the skin of the patient 16 near the wrist 14. The control module 22 can determine the predetermined amount of ultraviolet radiation as function of the patient's susceptibility to ultraviolet radiation. In one embodiment, the control module 22 can determine the patient's susceptibility to ultraviolet radiation as a function of the patient's skin pigmentation and skin thickness.

Determining the patient's susceptibility to ultraviolet radiation as a function of the patient's skin pigmentation and skin thickness can be ascertained using one of a number of different approaches. For example, a patient can enter information pertaining to their skin pigmentation and skin thickness manually via an input component that can be part of the control module 22 or a separate component that is configured to operate cooperatively with the control module 22. The manual input of information can contain specific answers to skin pigmentation and skin thickness queries or the input can include responses to a series of questions (e.g. race, weight, etc.) that the control module 22 can use to determine the patient's pigmentation type and skin thickness. In one embodiment, a visible camera can be used to obtain an image of the patient's skin about the wrist 14 of the patient 16. In this manner, the visible camera can send the image to the control module 22 for ascertaining the pigmentation and skin thickness about the body part (e.g. the wrist) of the patient 16. The visible camera can be used in other capacities with the wearable light phototherapy device 10. For example, the visible camera can be configured to obtain an image of the patient's skin about the wrist 14 of the patient 16 during and/or after receiving the predetermined amount of ultraviolet radiation from the ultraviolet light emitting source 20. The control module 22 can then ascertain changes in the skin color of the body part during and/or after the patient 16 has received the predetermined amount of ultraviolet radiation by comparing before irradiation images and during and/or after irradiation images.

The control module 22 can utilize other information to determine the patient's susceptibility to ultraviolet radiation. For example, the control module 22 can determine the patient's susceptibility to ultraviolet radiation as a function of a plurality of general patient parameters. The plurality of general patient parameters can include, but are not limited to, the patient's skin dryness, skin temperature, age, weight, gender and race. For example, differences in pigmentation can impact the ability of UVB to penetrate the outer layers of the skin. Also, weight and/or gender can impact daily Vitamin D requirements. It is understood that information pertaining to general patient parameters can be obtained through a variety of approaches. For example, an infrared camera can be configured to obtain an infrared image of the patient's skin about the wrist 14 of the patient 16. In this manner, the control module 22 can infer the skin temperature about the body part of the patient 16 from the infrared image. In another embodiment, information pertaining to the general patient parameters such as the age, the weight, the gender and the race of the patient 16 can be entered via the input component and used by the control module 22 to determine the patient's susceptibility to ultraviolet radiation, e.g., by comparison with data acquired from other patients with similar parameters.

In addition to data that pertains to skin pigmentation, skin thickness and the general patient parameters, other information such as the patient's existing medical conditions and/or medical history can be used to determine the patient's susceptibility to ultraviolet radiation. For example, if the patient has been diagnosed with a melanoma or other non-melanoma type skin cancers, then the control module 22 can use that information to select a specific type of radiation with a peak wavelength that does not exacerbate the skin cancer. The control module 22 can also specify irradiation parameters for the ultraviolet light emitting source 20 so that the radiation generated from the source delivers a treatment that is in accordance with guidelines for a person with a given medical condition and/or history.

These irradiation parameters which can be included as part of the predetermined amount of ultraviolet radiation specified by the control module can include, but are not limited to, a dosage setting of the ultraviolet radiation, an intensity setting of the ultraviolet radiation, a spatial coverage setting of the ultraviolet radiation applied to the body part of the patient, a spectral power distribution setting of the ultraviolet light emitting source 20, and a duration setting that the ultraviolet radiation is applied to the body part of the patient 16.

It is understood that the control module 22 can determine the patient's susceptibility to ultraviolet radiation based on various combinations of the aforementioned information. In particular, the control module 22 can use the different forms of information singly or in combination with one another to determine the patient's susceptibility to ultraviolet radiation. For example, the control module 22 can determine the patient's susceptibility to ultraviolet radiation based on the patient's skin pigmentation and skin thickness and the general patient parameters. In one embodiment, the control module 22 can determine the patient's susceptibility to ultraviolet radiation based on the general patient parameters and the patient's existing medical conditions and/or medical history.

The control module 22 can further include other components that further facilitate a phototherapy treatment and a cleaning treatment in instances when the wearable ultraviolet radiation phototherapy device 10 is unworn. As mentioned above, the control module 22 can include an input component that permits a user or patient to enter information prior to a treatment and during a treatment. For example, in addition to the aforementioned information, a patient can use the input component to activate and inactivate the operation of the ultraviolet light emitting source 20 as well as any other sources that may be used (e.g., visible light emitting source(s), infrared sources). In one embodiment, the input component can be used by the patient or other users (e.g., a medical provider) to manually adjust the predetermined amount of ultraviolet radiation delivered by the ultraviolet light emitting source. The input component can include a set of switches (e.g., on/off switches), a set of buttons, and/or a touch screen with user-defined selections to enable a user to specify various input selections regarding the operating parameters of the various treatments. In one embodiment, a button or a set of buttons can be used to toggle through a multitude of operating modes for selection of one of the modes. For example, a user can select a particular mode of operation by following a proper sequence of buttons and durations of pressure signals for these buttons.

The control module 22 can further include an output component such as for example, a visual display that can provide status information on the operation of the wearable ultraviolet light phototherapy device 10 and/or the treatment of the patient 16. For example, the output component can include an illuminating light display that is visible when the wearable ultraviolet light phototherapy device 10 is operational and not illuminated light when the device is off.

For clarity, both the input component and the output are neither depicted in FIG. 1 nor in any of the other embodiments described herein, however, it is understood that these components are presumed to be incorporated as components or functionalities associated with the control module 22. Nevertheless, those skilled in the art will appreciate that the input component and the output component can be implemented as separate components apart from the control module 22. The input component and output component can also take the form of one component that is configured to perform the functionalities of both. Further, the input component and the output component can be deployed on the exterior of the substrate (e.g., on the outer wall surface) 18 to allow a user ease of access and operation with these components.

Other components that can be incorporated in or operatively associated with the control module 22 include a timer (e.g., a dosage timer) with switches and/or the like, to manage the operation of the ultraviolet light emitting source 20 and any other sources (e.g., visible light emitting sources and infrared sources), as well as other components used to facilitate a phototherapy treatment and a cleaning treatment such as sensors. With the timer, the control module 22 can control the duration that the sources and sensors are activated and ensure that desired operating parameters including irradiation parameters are attained for that duration by making any necessary adjustments or modifications based on feedback obtained during the treatments. For example, the control module 22 operating in conjunction with the timer can manage the amount of time that the ultraviolet light emitting source 20 radiates in a pulsed mode of operation, or mange which sources operate at common or different peak wavelengths for different forms of radiation (e.g., UV-A, UV-B and UV-C).

The control module 22 can also include a wireless transmitter and receiver that is configured to communicate with a remote location via Wi-Fi, BLUETOOTH, and/or the like. In this manner, the patient 14 or a user can control the operation of the wearable ultraviolet light phototherapy device 10 with a smart phone. As used herein, a remote location is a location that is apart from the device 10. For example, a remote computer can be used to transmit operational instructions to the wireless transmitter and receiver. The operational instructions can be used to program functions performed and managed by the control module 22. In another embodiment, the wireless transmitter and receiver can transmit output results, data from sensors to the remote computer to attain an analysis of the wearable ultraviolet light phototherapy device 10 with regard to usage, quality of the treatments performed, and maintenance items that are necessary or impending.

The control module 22 can also include storage device capable of storing all of the data that is obtained during and after a phototherapy treatment and a cleaning operation. This capability enables the control module to statistically process the data, such as the history of the ultraviolet radiation intensity and duration, as well as the spectral power distribution of the ultraviolet radiation during the treatments. It is understood that the control module 22 can perform a multitude of other analyses of the data as desired.

The wearable light phototherapy device 10 can further include at least one sensor 24 to obtain operational data relating to the irradiation of the portion of skin near the wrist 14 of the patient 16. The sensors 24 can be located at various positions along the inner and outer wall surfaces of the substrate 18. It is understood that the location of the sensors 24 as well the number of sensors utilized are variable. In one embodiment, the sensor 24 is operatively coupled to the ultraviolet light emitting source 20 and the control module 22. In this manner, the control module 22 can control the operation of the ultraviolet light emitting source 20 as a function of the operational data detected by the sensor 24. In addition, the control module 22 and the sensors 24 can be used to monitor the irradiation of the skin near the body part (e.g., the wrist 14) of the patient 16 with the ultraviolet light emitting source 20. To this extent, the control module 22 can adjust the predetermined amount of ultraviolet radiation directed to the body part as function of the operational data obtained by the sensor 24.

The sensor 24 can include any of a number of different sensors. In one embodiment, the sensor 24 can include an ambient radiation sensor that is configured to obtain radiation conditions of an ambient environment surrounding the substrate 18. For example, if the ambient radiation sensor detects that the patient is outside on a sunny day with a moderate to high amount of ultraviolet radiation exposure (e.g., based on an ultraviolet scale index), then the control module 22 can decide that a phototherapy treatment is not necessary for the patient 16 as she or he will receive an adequate amount of ultraviolet radiation for the day that is sufficient to meet the needs of a prescribed treatment for the medical condition underlying the basis for the treatment. In another embodiment, if the ambient radiation sensor detects that the patient is inside and sheltered from ultraviolet radiation exposure, then the control module can then direct the ultraviolet light emitting source to direct ultraviolet radiation of a specified type within a peak wavelength range to a body part of the patient.

In one embodiment, the sensor 24 can include a fluorescent sensor that is configured to detect fluorescence emitted from the body part of the patient 16 after irradiation by the ultraviolet light emitting source 20. The control module 20 can use the detected fluorescence to determine changes in the patient's skin based on the detected fluorescence emitted from the body part using any solution.

Other types of sensors that can be used with the wearable ultraviolet light phototherapy device 10 include, but are not limited to, visible light sensors (e.g., visible cameras), temperature sensors (e.g., thermistors), pressure sensors, and chemical sensors. In one embodiment, a temperature sensor and a pressure sensor can be used to detect conditions of the environment (e.g., temperature, pressure, etc.) about the body part of the patient 16 that is enclosed in, surrounded by, or covered by the substrate 18. For example, a temperature sensor can be used to detect whether temperature in the substrate 18 exceeds a predetermined maximum temperature. In one embodiment, the control module 22 can power off the ultraviolet light emitting source 20 in response to detecting exceedingly high temperatures to prevent any further phototherapy treatment with the source until the temperature within the substrate 18 is within a sufficient temperature range.

The wearable ultraviolet light phototherapy device 10 can further include a power supply component 26 that is configured to power the ultraviolet light emitting source(s) 20, the control module 22, the sensor(s) 24 and any other components (e.g., visible light emitting source(s) and infrared source(s)) that can be used to facilitate a phototherapy treatment of a patient or a cleaning treatment of a surface of an object in instances when the device is an unworn state. The power supply component 26 can include any one of a number of different power sources. In one embodiment, the power supply component 26 can include a rechargeable battery that can be recharged from an external port. For example, a USB, a mini USB or other appropriate rechargeable port can be used to charge the battery. Other examples of power sources that can be used as the power supply component 26 can include, but are not limited to, one or more batteries, a vibration power generator that can generate power based on magnetic inducted oscillations or stresses developed on a piezoelectric crystal, and a super capacitor that is rechargeable. The power supply component 26 can be located in any of a number of different locations. For example, the power supply component 26 can be located within the body of the substrate 18 or on the outer wall surface of its exterior.

Other components that can form a part of the wearable ultraviolet light phototherapy device 10 include a set of electrical connectors to charge the device, transfer data, connect additional sensors, and/or the like. In one embodiment, the set of electrical connectors can be located about the substrate 18 at locations that can include, but are not limited to, the inner wall surface, the internal portion and the outer wall surface.

As mentioned above, the wearable ultraviolet light phototherapy device 10 can include other types of sources that can facilitate the phototherapy treatment of the patient. For example, the wearable ultraviolet light phototherapy device 10 can have other sources located about the substrate 18 such as a visible light emitting source (e.g., a visible light emitting diode, incandescent, a fluorescent, a laser, a solid state light source, and/or the like that emit radiation having a wavelength at least partially in a range of 400 nm to 700 nm), an infrared source, a heating source, a vibrational source, chemical treatment sources, and/or the like. The use and number of such sources will depend on the patient and the treatment that he or she is to have based on their current medical conditions and past medical conditions.

Instead of having the various components of the wearable ultraviolet light phototherapy device 10 such as the ultraviolet light emitting source 20, the control module 22, and the sensor 24 incorporated within the substrate 18, it is understood that other configurations can be utilized that enable operation of these components in a wearable article. For example, the ultraviolet light emitting source 20, the control module 22, the sensor 24, and any other components can be incorporated within a housing or enclosure that is coupled to the wearable article. In one embodiment, a housing having the ultraviolet light emitting source 20, the control module 22, and the sensor 24 can be removably attached to the inner wall surface of the substrate. In this manner, the housing can operate as a modular unit that is configured to provide a phototherapy treatment to the skin of a specific body part of the patient. It is understood that the housing can include a semi-flexible or flexible medium or material that is compatible with the substrate 18 in order to receive, slide over, wrap around, or adhere to, a body part. In this manner, the housing and the substrate can tightly adhere to the person's body, ensuring that ultraviolet radiation is not emitted into the ambient during a phototherapy treatment.

Figure 11:
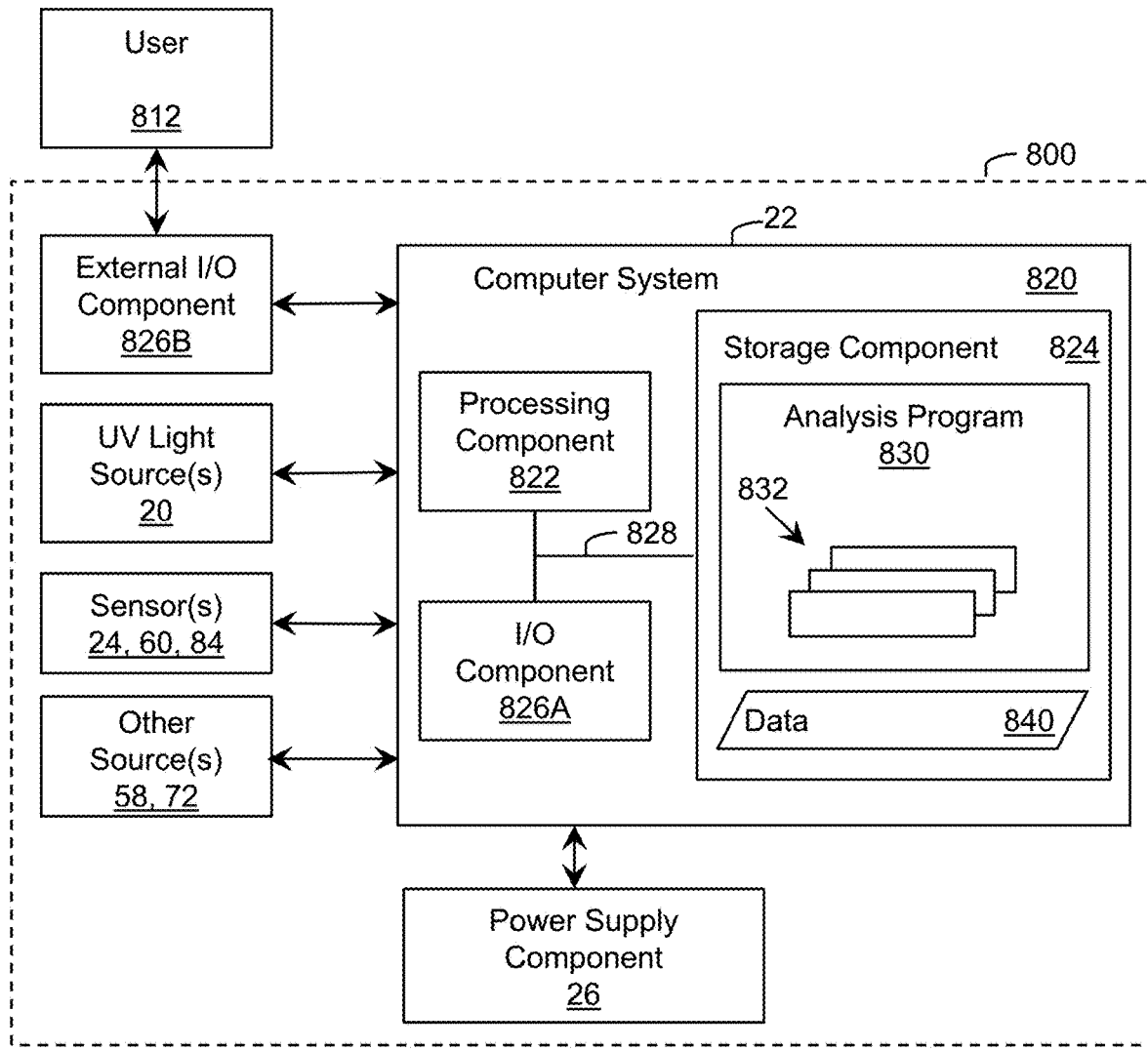
FIG. 11 shows a schematic block diagram representative of an overall processing architecture for a wearable ultraviolet light phototherapy device according to an embodiment of the present invention.

The aforementioned components of the wearable ultraviolet light phototherapy device 10 are illustrated in FIG. 11 and discussed further with regard to that figure. These components are also suitable for use with any of the other wearable ultraviolet light phototherapy devices that can be used with body parts including, but not limited to, the back, the leg, the neck, the arm, the fingers and the feet including toes. It is understood that the functions of these components can vary and will depend on the type of wearable article (e.g., rings, bracelets, patches, sleeves, etc.) that these components are utilized with and the body part that treatment is to be directed to.

Figure 2:
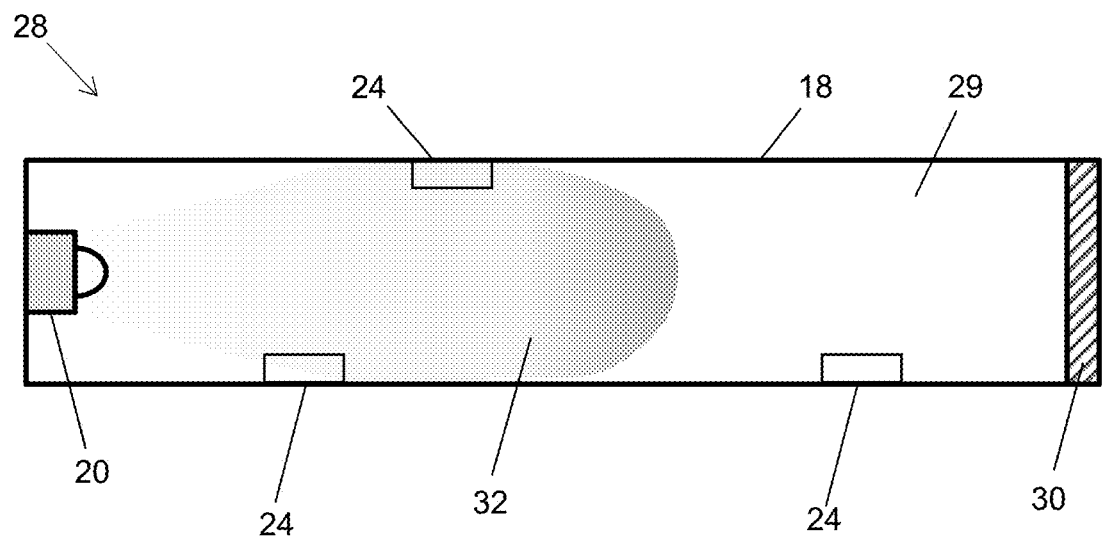
FIG. 2 shows a schematic of a wearable ultraviolet light phototherapy device in the form of a band according to an alternative embodiment of the present invention.

FIG. 2 shows a schematic of a wearable ultraviolet light phototherapy device 28 in the form of a band 29 according to an alternative embodiment of the present invention. The wearable ultraviolet light phototherapy device 28, which is shown in FIG. 2 in an extended view, unworn by a patient, includes a substrate 18, an ultraviolet light emitting source 20, and a set of sensors 24. Although not illustrated in FIG.

2, it is understood that the wearable ultraviolet light phototherapy device 28 can include a control module 22 and a power supply component 26. Also, it is understood that the number and location of each of the components (e.g., the ultraviolet light emitting source 20 and the sensors 24) as well as the specific type (e.g., UV-A light emitting source, UV-B light emitting source, visible light emitting source, ambient radiation sensor, fluorescent sensor) is variable. In addition, it is understood that the depiction of the band 29 that embodies the wearable ultraviolet light phototherapy device 28 as shown in FIG. 2 does not necessarily mean that it has to be incorporated into the whole band. For example, the band can be formed from a set of segmented units, wherein one or a few of the segments can be configured with the various components of the wearable ultraviolet light phototherapy device that facilitate the phototherapy treatment.

As shown in FIG. 2, the wearable ultraviolet light phototherapy device 28 can further include a reflecting element 30 that is configured to reflect ultraviolet radiation generated from the ultraviolet light emitting source 20 that propagates in the substrate 18. In one embodiment, the ultraviolet light emitting source 20 and the reflecting element 30 can be located at opposing ends of the substrate 18. In this manner, the ultraviolet light emitting source 20 can direct light that is partially parallel along the band direction, as indicated schematically by a light profile 32, towards the reflecting element 30. The reflecting element 30 can reflect the ultraviolet radiation back along the band direction of the substrate 18 where the light diffuses into the skin of the patient about the body part that the substrate is worn around. Having the reflecting element 30 located at an end opposing the ultraviolet light emitting source 20 can be beneficial in that fewer LED sources can deliver radiation to a larger surface area even in close proximity.

The reflecting element 30 can include one of any of a number of reflecting mechanisms. In one embodiment, the reflecting element 30 can include a mirror. Other reflecting elements can include, but are not limited to a truncated pyramid-shaped reflector, a parabolic reflector, a waveguide used in combination with other style reflectors, etc.

The reflecting element 30 can also include an ultraviolet reflective material. In one embodiment, all or at least portion of the inner wall surface of the substrate 18 can have an ultraviolet reflective material. In general, an ultraviolet reflective material with a reflection coefficient of at least 50% will enable recycling of the ultraviolet radiation generated from the ultraviolet light emitting source 20 for eventual diffusion into the skin of the patient. In one embodiment, the ultraviolet reflective layer can include polished aluminum, PTFE (e.g., Teflon®), expanding polytetrafluoroethylene (ePTFE), ETFE or combinations thereof. In another embodiment, the ultraviolet reflective material can include a diffusive ultraviolet reflective material. The diffusive ultraviolet reflective material can include a coating or thin film of a fluoropolymer. Examples of a fluoropolymer that are suitable as an ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like.

The wearable ultraviolet light phototherapy device 28 of FIG. 2 as well as any of the other devices described herein can include additional optical elements besides the reflecting element 30. For example, the wearable ultraviolet light phototherapy device 28 of FIG. 2 and any of the other devices described herein can include one or more optical elements to optically couple the ultraviolet radiation along the band direction to various locations of the substrate. In one embodiment, the optical element(s) can be placed in proximity to the ultraviolet light emitting source(s) 20. For example, the optical element(s) can be placed in the substrate 18 about at least a portion of its inner wall surface. The optical element(s) can include, but is not limited to, one or more of a lens, a parabolic mirror, a prism, non-mirror reflective surfaces, and/or combinations thereof.

Figure 3:
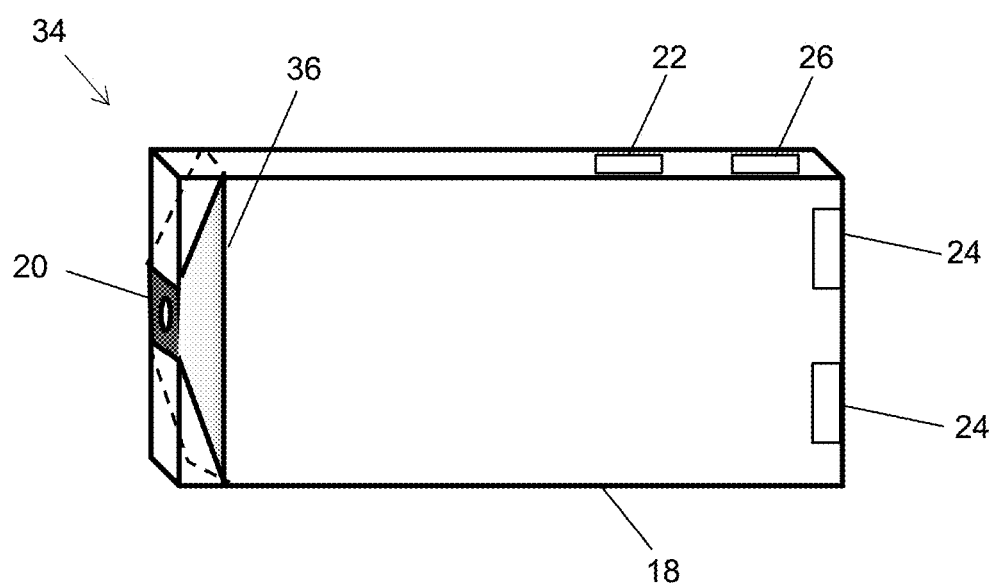
FIG. 3 shows a schematic of a wearable ultraviolet light phototherapy device in the form of a band according to another alternative embodiment of the present invention.

As noted above, the location of each of the components (e.g., the ultraviolet light emitting source 20, the sensors 24, the reflecting element 30) with regard to the substrate 18 of the wearable ultraviolet light phototherapy device 28 is variable, and thus, the embodiment depicted in FIG. 2 is not meant to be limiting to the possibility of arrangements of these components. For example, instead of having the reflecting element 30 at an end opposing the ultraviolet light emitting source 20, it can be located in a different position. In one embodiment, as shown in FIG. 3, the substrate 18 of a wearable ultraviolet light phototherapy device 34 can have a truncated pyramid-shaped reflector 36 optically coupled to the ultraviolet light emitting source 20 and a set of sensors 24 at an opposing end of the substrate 18. In one embodiment, the ultraviolet light emitting source 20 can be positioned within the truncated pyramid-shaped reflector 36. In this manner, the light can be directed along the band where the irradiation parameters of the ultraviolet light emitting source 20 can be controlled by the operation of the control module 22 and the set of sensors 24, all of which are powered by the power supply component 26.

Figure 4:
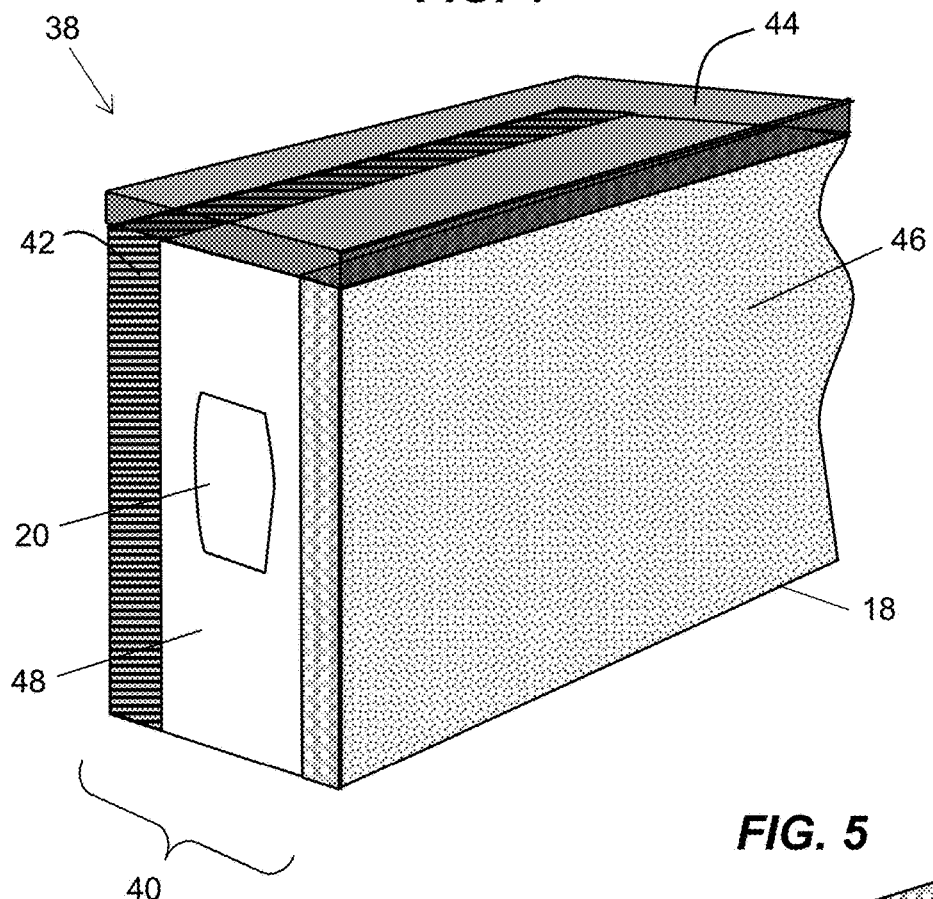
FIG. 4 shows a schematic of a wearable ultraviolet light phototherapy device having a substrate formed from a multi-layered structure according to an embodiment of the present invention.

The substrate 18 of any of the wearable ultraviolet light phototherapy devices described herein can be formed from a multi-layered structure with at least one layer coupled to one or more ultraviolet light emitting sources 20 that is transparent to ultraviolet radiation, and capable of light guiding radiation along a band or one of another of the wearable articles described herein that can incorporate the features of the various embodiments. FIG. 4 shows a schematic of a wearable ultraviolet light phototherapy device 38 having a substrate 18 formed from a multi-layered structure 40 according to an embodiment of the present invention. As shown in FIG. 4, the multi-layered structure 40 of the substrate 18 can have a reflective outer layer 42 including a reflective side layer 44, a diffusive layer 46, and a core layer 48 positioned between the reflective outer layer and the diffusive layer. The core layer 48 can be coupled to the ultraviolet light emitting source 20. It is understood that the ultraviolet light emitting source 20 can be located in positions other than the side location depicted in FIG. 4. For example, the ultraviolet light emitting source 20 can be can be located on either a lateral side of the core layer 48 or even positioned in the middle or internal portion of the core layer 48 directed towards the diffusive layer 46. With this configuration, the core layer 48 can light guide the ultraviolet radiation generated from the light emitting source 20 in a lateral direction (i.e., along the direction of the substrate), while the reflective outer layer 42 and the reflective side layer 44 can reflect the ultraviolet radiation generated from the ultraviolet light emitting source 20 towards the diffusive layer 46 for transmission into a body part of the patient.

The reflective outer layer 42 and the reflective side layer 44 can include an ultraviolet reflective material that enables recycling of the ultraviolet radiation generated from the ultraviolet light emitting source(s) 20. For example, any of the aforementioned ultraviolet reflective materials are suitable for use with the reflective outer layer 42 and the reflective side layer 44.

In one embodiment, the core layer 48 can comprise an ultraviolet transparent layer. A transparent fluoropolymer material is one type of material that can be used in the ultraviolet transparent layer. Examples of a transparent fluoropolymer material can include, but is not limited to, EFEP, FEP, PTFE, ECTFE, PCTFE, PFA, PVDF, ETFE, THV, LDPE and MFA. In one embodiment, the ultraviolet transparent layer can include an ultraviolet transparent fluid such as, for example, distilled water, purified water as defined by the U.S. Food and Drug Administration, and water that is sufficiently clean for human consumption (potable water). In one embodiment, the ultraviolet transparent fluid can include a transparent gas.

The core layer 48 can include other forms and is not meant to be limited to an ultraviolet transparent layer. For example, at least a portion of the core layer 48 can include voids, openings or spaces formed between the reflective outer layer 42 and the diffusive layer 46. In one embodiment, the core layer 48 can define a void formed between the reflective outer layer 42 and the diffusive layer 46.

The diffusive layer 46 can include an ultraviolet transparent diffusive layer that promotes transmission of the light from the ultraviolet light emitting source 20 into the skin of the patient. Examples of an ultraviolet transparent diffusive layer can include, but is not limited to, $SiO_2$, $Al_2O_3$, $CaF_2$, $MgF_2$, and/or the like. The diffusive layer 46 can include a layered arrangement of fluoropolymer films, voids, and/or light diffusing elements.

Figure 5:
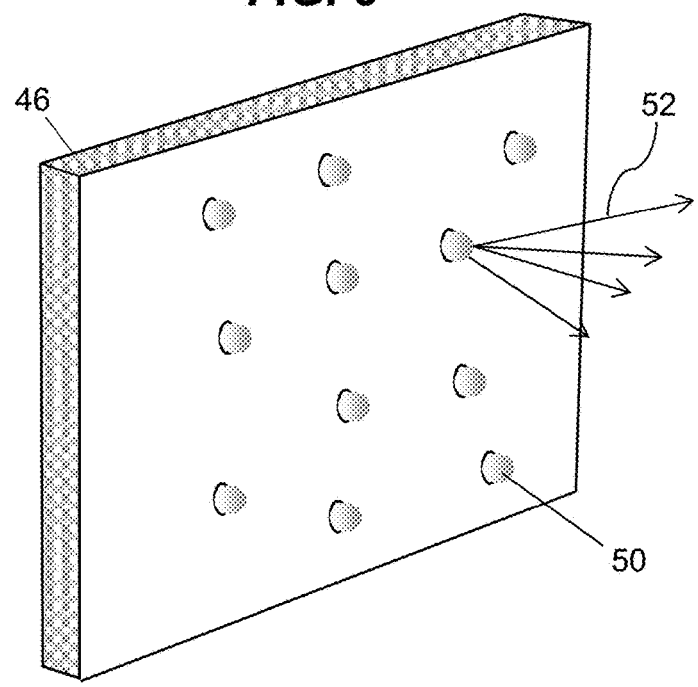
FIG. 5 shows one of the layers of the multi-layered structure of the wearable ultraviolet light phototherapy device depicted in FIG. 4 with a diffusive layer having ultraviolet transparent protrusions according to an embodiment of the present invention.

The diffusive layer 46 can include additional elements that aid in the extraction of the ultraviolet radiation from the substrate 18 into the skin of the patient. In one embodiment, as depicted in FIG. 5, the diffusive layer 46 can include a plurality of ultraviolet transparent protrusions 50 configured to extract the ultraviolet radiation 52 from the core layer for transmission into the body part of the patient via the diffusive layer 46. As used herein, an ultraviolet transparent protrusion is any structure that facilitates scattering and dispersal of ultraviolet radiation emitted from an ultraviolet light emitting source. The ultraviolet transparent protrusions 50 can be arranged on the exterior surface of the diffusive layer 46 in one of a number of arrangements. For example, the ultraviolet transparent protrusions 50 be configured to distribute the ultraviolet radiation in a uniform pattern and/or in a non-uniform pattern. Note that the amount of ultraviolet transparent protrusions 50 located on the exterior surface of the diffusive layer 46 can vary depending on the direction and the pattern of the ultraviolet radiation that is desired. For example, in one embodiment, a greater amount of ultraviolet transparent protrusions 50 can be concentrated on a portion of the diffusive layer 46 that is centrally located with respect to a part of the skin of the patient that is desired to have a higher amount of light directed theretoward.

The ultraviolet transparent protrusions 50 are illustrated in FIG. 5 in the form of small cylindrical-shaped knobs, however, other shapes and sizes are within the scope of the various embodiments of the present invention. In one embodiment, the ultraviolet transparent protrusions 50 can be formed from material that includes an ultraviolet transparent material, such as a fluoropolymer material, fused silica, and/or the like. Other examples of materials that are suitable for use with the ultraviolet transparent protrusions 50 can include, but are not limited to, an ultraviolet reflective expanded polytetrafluoroethylene (ePTFE) membrane (e.g., GORE® Diffuse Reflector Material), and/or the like.

In place of the aforementioned multi-layered structure, the substrate 18 can include a light guiding layer or media formed from any of the previously mentioned fluoropolymers to light guide the radiation along the band. In this manner, the light guiding layer can utilize total internal reflection (TIR) to propagate the light along the direction of the band to deliver the light to the skin of the patient 16. In one embodiment, the light guiding layer can be placed between the skin of the patient and the substrate. In one embodiment, the ultraviolet light emitting source(s) 20 can be located between the substrate and light guiding layer. In another embodiment, the ultraviolet light emitting source(s) 20 can be partly or fully immersed into the light guiding layer.

Instead of being formed with the substrate 18, the light guiding layer can be a component separate from the substrate. For example, the light guiding layer can be attached, affixed, adhered, fastened, secured, and the like, to the substrate 18. For example, the light guiding layer can have fastening mechanisms, such as snaps or clips, molded into the material to attach to the substrate, or could be designed with threads and screw onto the substrate. To this extent, the light guiding layer can function as a removable and replaceable media with respect to the substrate 18.

Figure 6:
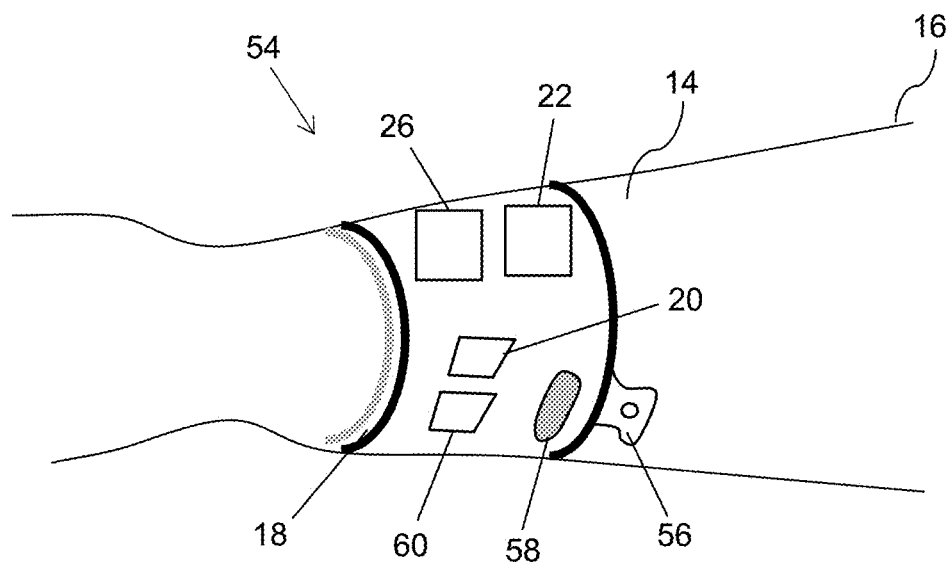
FIG. 6 shows a wearable ultraviolet light phototherapy device that receives a body part of a patient and tightly conforms to the shape and contours of the body part according to an embodiment of the present invention.

FIG. 6 shows a wearable ultraviolet light phototherapy device 54 according to another embodiment where the substrate 18 of the device can be received by a body part of a patient 16 such as their wrist 14 so that it tightly conforms to the shape and contours of the wrist. In this embodiment, the wearable ultraviolet light phototherapy device 54 can include an ultraviolet light emitting source 20 operating in conjunction with a visible camera 56, an infrared source 58, and a fluorescent sensor 60, all powered by a power supply component 26 and controlled by a control module 22. It is understood that the configuration of components as depicted in FIG. 6 represents only one possible arrangement and is not meant to limit this embodiment or any others described herein. For example, other sources can be deployed such as a visible light emitting source, as well as other sensors such as an ambient radiation sensor and a temperature sensor. Further, the number and placement of these components are representative of only one possibility and is not meant to limit the embodiment depicted in FIG. 6 nor any other embodiment described herein.

The wearable ultraviolet light phototherapy device 54 can be configured to operate in a number of possible ways. For example, before initiating a phototherapy treatment, the visible camera 56 can obtain an image of the patient's skin about the wrist 14 of the patient 16. The visible camera 56 can then send the image to the control module 22 for ascertaining the pigmentation and skin thickness about the wrist 14 of the patient 16. The infrared camera 58 can be used to obtain an infrared image of the patient's skin about the wrist 14 of the patient 16. The control module 22 can infer the skin temperature about the body part of the patient 16 from the infrared image. With the skin thickness and the skin temperature information and any information inputted by the patient 16 through the input component such as the age, the weight, the gender, the race and the medical conditions and history, the control module 22 can determine a specific type of radiation (e.g., UV-A and/or UV-B radiation) with a peak wavelength as well as specify other irradiation parameters (e.g., a dosage setting, an intensity setting, a spatial coverage setting, a spectral power distribution setting, and a duration setting) for irradiating the patient 16 in a phototherapy treatment. The control module 22 can then direct the ultraviolet light emitting source 20 to irradiate the patient 16 according to the determined parameters. Note that the patient 16 can use the input component to override these settings and specify their own irradiation parameters.

During the phototherapy treatment, the control module 22 can monitor the irradiation of the skin near the wrist 14 of the patient 16 as a function of the operational data detected by the fluorescent sensor 60 and control the operation of the ultraviolet light emitting source 20 based on the fluorescence emitted from the wrist after irradiation. In this manner, the control module 22 can adjust the amount of ultraviolet radiation directed to the wrist 14 along with any of the other irradiation parameters that achieve the desired modification. In addition, the patient 16 also can have the option to utilize the control module 22 to manually make modifications to the irradiation by the light emitting source 20.

In one embodiment, the visible camera 56 can be used to obtain an image of the patient's skin about the wrist 14 of the patient 16 during the phototherapy treatment. If the control module 22 determines that there are changes in the skin color of the wrist 14 that show the patient is receiving too much ultraviolet radiation, then it can adjust the amount of radiation emitted from the ultraviolet light emitting source 20 and if need be shut off the source from further operation.

In one embodiment, the infrared source 58 can be used to obtain an infrared image of the patient's skin about the wrist 14 of the patient 16 during the phototherapy treatment. The control module 22 can use this image to determine changes in the temperature and/or the humidity about the wrist 14. If the control module 22 determines that there are changes in the temperature and/or the humidity about the wrist 14 that indicate that the skin about the wrist is too hot or wet, then the control module can adjust the amount of radiation emitted from the ultraviolet light emitting source 20, and if need be shut off the source until it determines that these conditions no longer exist.

Figure 7:
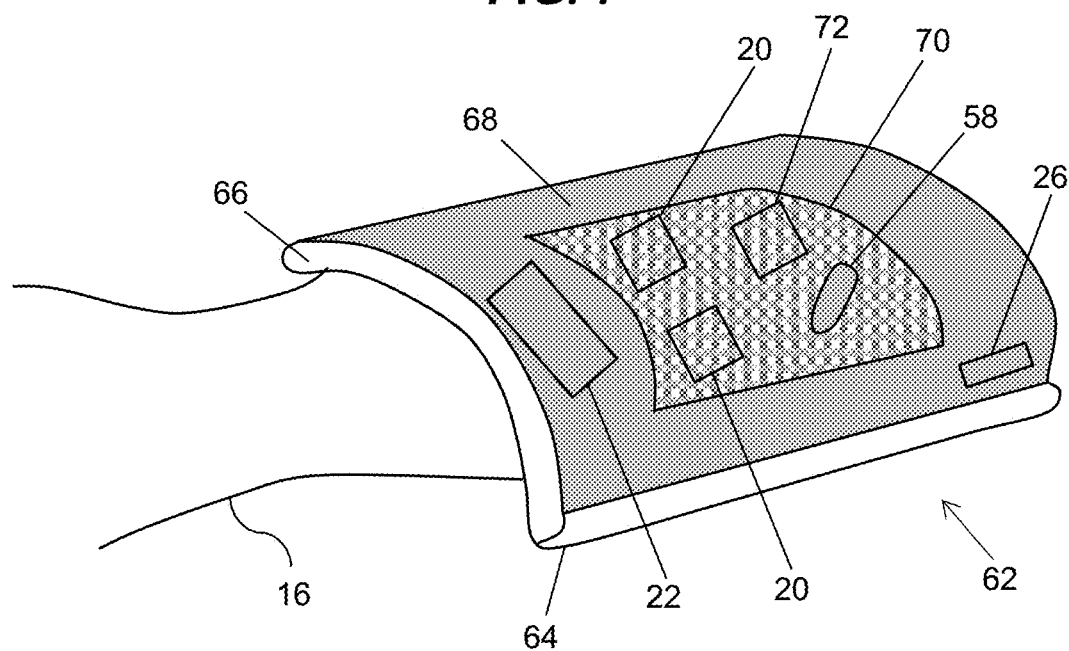
FIG. 7 shows a wearable ultraviolet light phototherapy device that is secured to a body part of a patient according to an embodiment of the present invention.

FIG. 7 shows a wearable ultraviolet light phototherapy device 62 according to another embodiment where the device can be received by a body part of a patient 16 in a manner that it tightly conforms to the shape and contours of the part. As with other embodiments, the wearable ultraviolet light phototherapy device 62 includes a substrate 64 that can be wrapped around, pulled over, secured to, or adhered to the body part of the patient 16. However, in this embodiment, the sources (e.g., the ultraviolet light emitting sources, visible light emitting sources, and infrared sources) can be separated from the skin by a skin separating material 66. The skin separating material can include a padding, cushioning, filling, liner, or the like, that can be tightly secured to the patient 16 such that the material tightly conforms to the shape and contours of a particular body part.

The skin separating material 66 can be formed from any suitable material that can conform to the shape of the body part and contain (e.g., absorb, reflect, and/or the like) ultraviolet radiation. In one embodiment, the skin separating material 66 can include an ultraviolet reflecting material that reflects ultraviolet radiation towards the skin of the body part, while absorbing radiation from leaking out of an exterior surface 68 of the substrate 64 into the ambient environment. To this extent, the skin separating material can include two or more layers of material, such as an ultraviolet reflective layer and an ultraviolet absorbing layer.

As shown in FIG. 7, the substrate 64 can include a source region 70 having one or more ultraviolet light emitting sources 20 and any other sources that can facilitate a phototherapy treatment of the patient 16, including but not limited to, a visible light emitting source 72, an infrared source 58, etc. With the separation from the skin of the patient 16, the source region 70 can be slightly elevated from the particular body part. Although not depicted in FIG. 7, the source region 70 can include a window that enables transmission of the particular type radiation generated from each of the various sources towards the skin of the patient 16. The source region 70 can also include a diffusive layer that facilitates transmission and dispersal of the radiation from the various sources into the skin of the patient 16. The diffusive layer, which can be formed from any of the aforementioned diffusive material, can direct the radiation into the skin of the patient in a particular direction, pattern, and or depth.

Other components not depicted in the wearable ultraviolet light phototherapy device 62 of FIG. 7 can include one or more of any of the aforementioned sensors. In this manner, the control module 22, the sources and the sensors, all of which can be powered by the power supply component 26, can be used to control the phototherapy treatment provided to the patient 16 as described herein. Also, the exterior surface 68 of the substrate 64 can include an input component for entering a variety of information pertaining to the phototherapy treatment of the patient 16 and an output component that can display information to the patient 16 with respect to the treatment.

The wearable ultraviolet light phototherapy devices described herein have been described as only a solitary unit in use with a patient, however, it is understood that the patient can wear more than one of the devices at a time. For example, the patient can wear a number of the wearable ultraviolet light phototherapy devices with different body parts. In one embodiment, the patient can use a set of different wearable ultraviolet light phototherapy devices with each device worn over a different body part. The control modules of each wearable ultraviolet light phototherapy device can be coordinated to deliver a dose of ultraviolet radiation such that the patient receives a total overall dose of ultraviolet radiation that satisfies a predetermined amount specified for the patient for a particular treatment. The sensors associated with each of the wearable ultraviolet light phototherapy devices can be used to monitor the irradiation of the patient and control the amount of radiation from each device as needed to ensure that the patient receives the specified total dosage for the treatment. It is understood that the control modules of each of the wearable ultraviolet light phototherapy devices can operate independently or at the behest of a centralized remote control unit or another device such as a smart phone. Further, it is understood that the wearable ultraviolet light phototherapy devices in this embodiment are not meant to be limited to one particular type of device, but instead it is possible to have the patient wear a multiple of different types of devices during a particular phototherapy treatment.

Figure 8A:
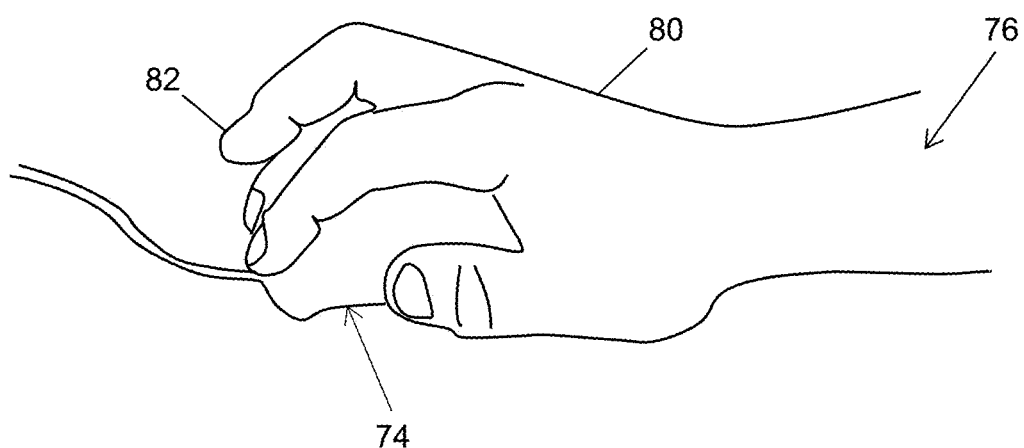
FIGS. 8A-8B show a wearable ultraviolet light phototherapy device in the form of a hand-held pointing device according to an embodiment of the present invention.
Figure 8B:
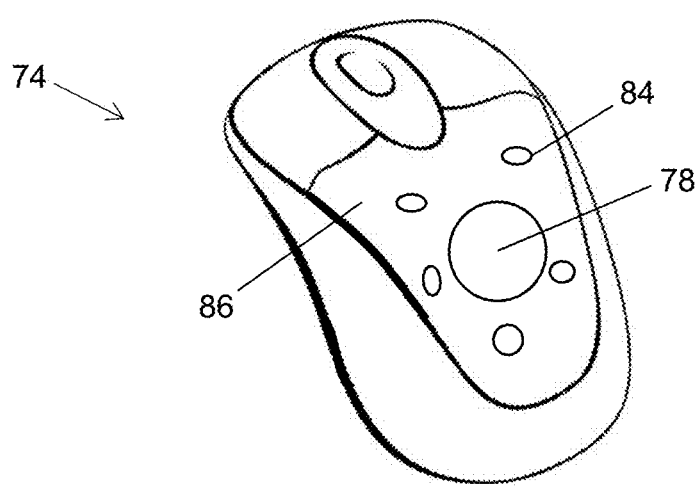

FIGS. 8A, 8B, 9A, and 9B show examples of other ultraviolet light phototherapy devices incorporated into electronic devices that can form wearable ultraviolet light phototherapy devices as defined herein. In particular, FIGS. 8A and 8B show a wearable ultraviolet light phototherapy device 74 that can function as a hand-held pointing device and also provide a phototherapy treatment to a user 76 of the hand-held pointing device. As shown in FIGS. 8A and 8B, the hand-held pointing device can be a computer mouse, however, it is understood that other hand-held pointing devices used with computer related devices are equally suitable for incorporation with the aforementioned componentry of any of the various embodiments such as trackballs, joysticks, and the like.

In the embodiment depicted in FIGS. 8A and 8B, the wearable ultraviolet light phototherapy device 74 can include a light emitting region 78 to irradiate the underlying portion of the user's 76 hand 80 including fingers 82. Although not shown in FIG. 8B, the light emitting region 78 can include all of the aforementioned components to implement a phototherapy treatment such as for example, at least one ultraviolet light emitting source, a visible light emitting source, an infrared source, and sensors (e.g., fluorescent sensor, temperature sensor, etc.) to monitor the phototherapy treatment of the user 76. It is also understood that the wearable ultraviolet light phototherapy device 74 can include a control module to control and monitor the phototherapy treatment in the aforementioned manner, as well as an input and output component to enter and receive information pertaining to the operation of the treatment. Also, the light emitting region 78 can also include a diffusive layer that can direct the radiation into the skin of the user (e.g., the hand 80 and fingers 82) in a particular direction, pattern, and or depth.

In one embodiment, the wearable ultraviolet light phototherapy device 74 can include at least one pressure sensor 84 located on a top surface 86 of the hand-held pointing device dispersed about the light emitting region 78. In this manner, the pressure sensors 84 can detect the pressure of the user's 76 hand 80 on the hand-held pointing device and send signals representative of the detected pressure conditions to the control module. The control module can activate the sources and initiate a phototherapy treatment on determining that pressure conditions about the hand-held pointing device satisfy a predetermined pressure threshold indicative of the presence of the user's 76 hand 80 on the hand-held pointing device. Similarly, the control module can terminate the phototherapy treatment upon receiving signals from the pressure sensors 84 that the user 76 has removed his or her hand from the hand-held pointing device. In comparison to some of the aforementioned embodiments, the wearable ultraviolet light phototherapy device 74 makes administering a phototherapy treatment into the skin of a person more versatile as he or she can be irradiated indoors in an office setting while still being able perform other functions. For example, the user can continue to perform the work at the computer terminal while receiving a phototherapy treatment.

Figure 9A:
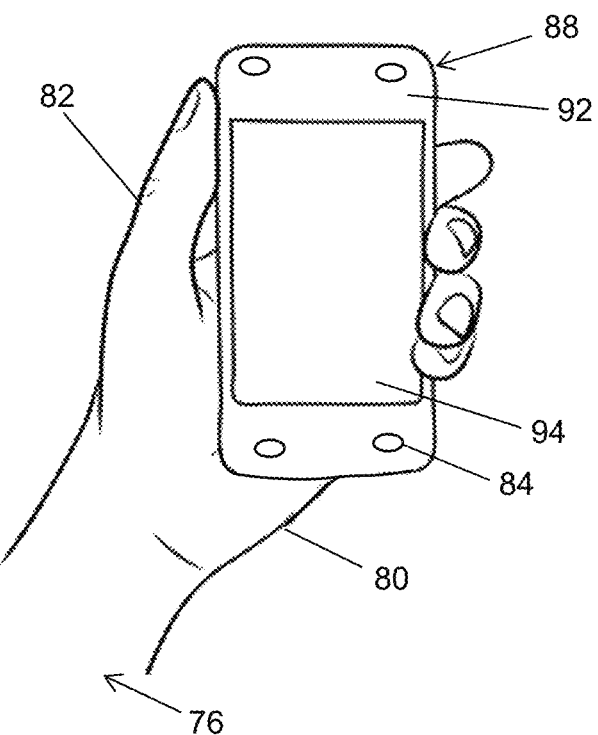
FIGS. 9A-9B show a wearable ultraviolet light phototherapy device in the form of a mobile phone according to an embodiment of the present invention.
Figure 9B:
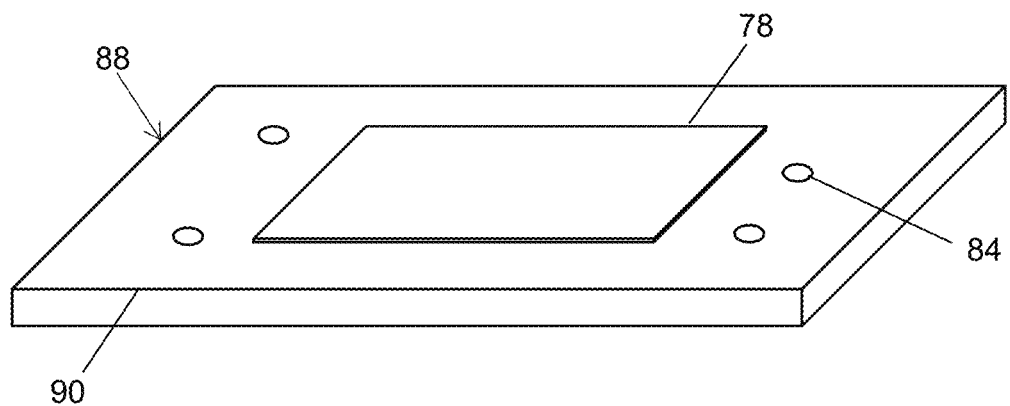

FIGS. 9A and 9B show an example of a wearable ultraviolet light phototherapy device 88 that can function as a hand-held electronic device and also provide a phototherapy treatment to a user 76 of the electronic device. As shown in FIGS. 9A and 9B, the hand-held electronic device can be a mobile phone (e.g., a cell phone, smart phone, etc.), however, it is understood that other hand-held electronic devices are equally suitable for incorporation with the aforementioned componentry in order to implement a phototherapy treatment. In addition, accessories associated with these hand-held electronic devices can incorporate the componentry. For example, the componentry of any of the various embodiments can be incorporated into a cover, a casing or the like (e.g., a cover for a smart phone), such that the cover can be used to perform a phototherapy treatment when placed over the hand-held electronic device.

The wearable ultraviolet light phototherapy device 88 of FIGS. 9A and 9B can also include a light emitting region 78 to irradiate the underlying portion of the user's 76 hand 80 including fingers 82. In one embodiment, the light emitting region 78 can be located on a backside 90 of the hand-held electronic device. Like the wearable ultraviolet light phototherapy device 74 of FIGS. 8A and 8B, the light emitting region 78 in FIGS. 9A and 9B can include all of the aforementioned components to implement a phototherapy treatment such as for example, at least one ultraviolet light emitting source, a visible light emitting source, an infrared source, and sensors (e.g., fluorescent sensor, temperature sensor, ambient radiation sensor, etc.) to monitor the phototherapy treatment of the user 76. It is also understood that the wearable ultraviolet light phototherapy device 88 can also include a control module to control and monitor the phototherapy treatment, as well as an input and output component to enter and receive information pertaining to the operation of the treatment. Also, the light emitting region 78 can also include a diffusive layer that can direct the radiation into the skin of the patient (e.g., into the hand 80 including fingers 82).

The wearable ultraviolet light phototherapy device 88 can also include at least one pressure sensor 84 located on the backside 90 of the hand-held electronic device dispersed about the light emitting region 78. In one embodiment, the pressure sensors 84 can be used to detect the pressure of the user's 76 hand 80 on the backside 90 of the hand-held electronic device and send signals representative of the detected pressure conditions to the control module. Similar to the embodiment depicted with regard to FIGS. 8A and 8B, the control module can activate the sources and initiate a phototherapy treatment on determining that pressure conditions about the hand-held electronic device satisfy a predetermined pressure threshold indicative of the presence of the user's 76 hand 80 on the hand-held electronic device. Similarly, the control module can terminate the phototherapy treatment upon receiving signals from the pressure sensors 84 that the user 76 has removed his or her hand from the hand-held pointing device.

As shown in FIG. 9A, a front side 92 of the hand-held electronic device can have pressure sensors 84 located about a display screen 94 of the hand-held electronic device. In one embodiment, pressure sensors 84 on the front side 92 of the hand-held electronic device control can be used to detect the presence of a cover placed over the display screen 94. In operation, the pressure sensors 84 can send signals representative of the detected pressure or proximity conditions of the cover with respect to the display screen 94 and send those signals to the control module. The control module can activate the sources and initiate a phototherapy treatment on determining that pressure conditions about the display screen 94 indicate that a cover has been secured over the screen. Alternatively, the control module can terminate the phototherapy treatment upon receiving signals from the pressure sensors 84 that the cover has been removed from the display screen.

Any of the various wearable ultraviolet light phototherapy devices described herein can be used in an unworn state to facilitate a cleaning treatment (e.g., cleaning, disinfection, sanitization) of a surface of an item or an object that has been contaminated with microorganisms, bacteria, viruses and the like. In order to effectuate a cleaning treatment, the wearable ultraviolet light phototherapy devices can have a UV-C light emitting source that can generate ultraviolet radiation with a peak wavelength ranging from 100 nm to 280 nm. In one embodiment, the UV-C light emitting source can generate ultraviolet radiation for disinfection that is in the range of 270 nm to 290 nm. In order to operate the wearable ultraviolet light phototherapy devices in such a manner to deliver a cleaning treatment, the devices need to be in an unworn state. In this manner, the user can direct the control module to activate the UV-C source via an input component in order to perform a cleaning treatment. The user, holding the device can then focus the beam emanating from the UV-C source toward the surface of the item or object that he or she desires to have cleaned.

Figure 10:
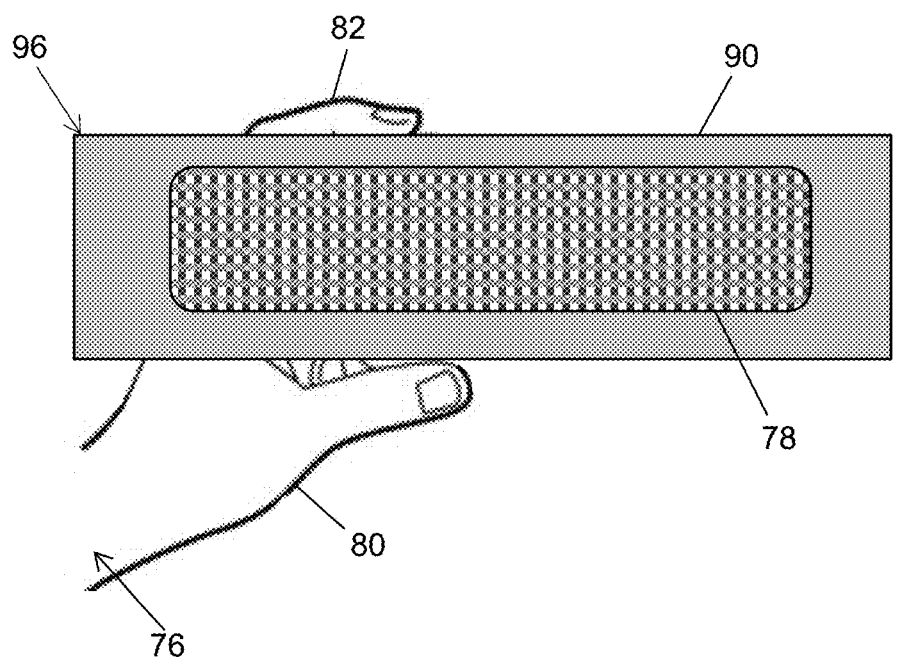
FIG. 10 shows a wearable ultraviolet light phototherapy device in the form of a hand-held electronic device that is suitable for performing a disinfection treatment in an unworn state according to an embodiment of the present invention.

FIG. 10 shows a wearable ultraviolet light phototherapy device 96 in the form of a hand-held electronic device that is suitable for performing a disinfection treatment in an unworn state according to an embodiment of the present invention. The wearable ultraviolet light phototherapy device 96 can take the form of a hand-held electronic device like a mobile phone, however, it is understood that other hand-held electronic devices can be implemented with componentry that enables the performance of both a phototherapy treatment and a cleaning treatment.

As shown in FIG. 10, the wearable ultraviolet light phototherapy device 96 can include a light emitting region 78 with a diffusive layer on the backside of 90 of the hand-held electronic device that can direct the radiation in a particular direction and pattern. In this manner, the user 76 can hold the hand-held electronic device and direct the ultraviolet radiation towards a surface of a particular object for cleaning. Although not depicted in FIG. 10, it is understood that the wearable ultraviolet light phototherapy device 96 can include all of the aforementioned components that can implement both a phototherapy treatment and a cleaning treatment such as for example, at least one ultraviolet light emitting source, a visible light emitting source, an infrared source, sensors, a control module with input and output components to control the operations.

FIG. 11 shows a schematic block diagram representative of an overall processing architecture 800 of a wearable ultraviolet light phototherapy device that can an implement a phototherapy treatment and a cleaning treatment that is applicable to any of the devices described herein. In this embodiment, the architecture 800 is shown including the ultraviolet light emitting source(s) 20, other sources 58, 72 (e.g., visible light emitting sources, infrared sources) and the sensors 24, 60, 84 for the purposes of illustrating the interaction of all of the components that can be used to provide a phototherapy treatment and a cleaning treatment.

As depicted in FIG. 11 and described herein, the processing architecture 800 of the wearable ultraviolet light phototherapy device can include a control module 22. In one embodiment, the control module 22 can be implemented as a computer system 820 including an analysis program 830, which makes the computer system 820 operable to manage the sources in the manner described herein. In particular, the analysis program 830 can enable the computer system 820 to operate the ultraviolet light emitting sources 20 to generate and direct ultraviolet radiation towards the skin of a body part of the patient and process data corresponding to one or more attributes regarding the irradiation, which can be acquired by the sensors 24, 60, 84. The computer system 820 can control each source and sensor individually or as a group.

In an embodiment, during an initial period of operation, the computer system 820 can acquire data from at least one of the sensors regarding one or more attributes of the irradiation and generate data 840 for further processing. The data 840 can include information regarding a presence of biological activity (e.g., microorganisms, viruses, bacteria, and/or the like) on a surface, an amount of radiation (e.g., ultraviolet, infrared, visible, and/or microwave) detected, and/or the like. The computer system 820 can use the data 840 to control one or more aspects of the irradiation by the various sources.

Furthermore, one or more aspects of the operation of the sources can be controlled or adjusted by a user 812 via an external I/O component 826B. The external I/O component 826B can be located, for example, on the exterior of any of the aforementioned wearable ultraviolet light phototherapy devices and used to allow the user 812 to selectively turn on/off the sources.

The external I/O component 826B can include, for example, a touch screen that can selectively display user interface controls, such as control dials, which can enable the user 812 to adjust one or more of: an intensity, scheduling, and/or other operational properties of a set of ultraviolet light emitting sources (e.g., operating parameters, radiation characteristics). In an embodiment, the external I/O component 826B could conceivably include a keyboard, a plurality of buttons, a joystick-like control mechanism, and/or the like, which can enable the user 812 to control one or more aspects of the operation of the set of sources. The external I/O component 826B also can include any combination of various output devices (e.g., an LED, a visual display), which can be operated by the computer system 820 to provide status information pertaining to a treatment for use by the user 812. For example, the external I/O component 826B can include one or more LEDs for emitting a visual light for the user 812, e.g., to indicate a status of the treatment. In an embodiment, the external I/O component 826B can include a speaker for providing an alarm (e.g., an auditory signal), e.g., for signaling that ultraviolet radiation is being generated or that a treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control module, the sources and the sensors. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively. In another embodiment, the control module can be implemented without any computing device, e.g., using a closed loop circuit implementing a feedback control loop in which the outputs of one or more sensors are used as inputs to control the operation of a treatment. Illustrative aspects of the invention are further described in conjunction with the computer system 820. However, it is understood that the functionality described in conjunction therewith can be implemented by any type of monitoring and/or control system.

Regardless, when the computer system 820 includes multiple computing devices, the computing devices can communicate over any type of communications link. Furthermore, while performing a process described herein, the computer system 820 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 11 can receive power from a power supply component 26. The power component 26 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

While shown and described herein as a device, a system and a method, it is understood that aspects of the present invention further provide various alternative embodiments. For example, in one embodiment, the various embodiments of the present invention can include a computer program fixed in at least one computer-readable medium, which when executed, enables a computer system to facilitate the ultraviolet irradiation of fluids. To this extent, the computer-readable medium includes program code, such as the analysis program 830, which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the present invention can provide a method of providing a copy of program code, such as the analysis program 830, which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the present invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the various embodiments of the present invention can implement a method that facilitates a phototherapy treatment and a cleaning treatment. This can include configuring a computer system, such as the computer system 820, to implement a method for facilitating the treatments. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of the various aspects of the present invention has been presented for purposes of illustration and description. It is not intended to be exhaustive or to limit the various embodiments of the present invention to the precise form disclosed, and obviously, many modifications and variations are possible. Such modifications and variations that may be apparent to an individual in the art are considered to fall within the scope of the various embodiments of the present invention.

What is claimed is:

1. A wearable ultraviolet light phototherapy device, comprising:
   a substrate configured to be worn on a body part of a patient, wherein the substrate comprises a multi-layered substrate including a reflective outer layer and a reflective side layer;
   a set of ultraviolet light emitting sources located about the substrate, the set of ultraviolet light emitting sources configured to deliver ultraviolet radiation, wherein at least one ultraviolet light emitting source in the set of ultraviolet light emitting sources includes an ultraviolet-B (UV-B) light emitting source that emits UV-B radiation having a peak wavelength ranging from 295 nm to 315 nm, and wherein at least one ultraviolet light emitting source in the set of ultraviolet light emitting sources includes an ultraviolet-C (UV-C) light emitting source that emits UV-C radiation having a peak wavelength ranging from 100 nm to 280 nm; and a control module coupled to the set of ultraviolet light emitting sources to control the operation thereof, wherein the controlling includes operating only the UV-B light emitting source during a phototherapy treatment mode when the substrate is in a worn state on the body part and operating only the UV-C light emitting source during a cleaning treatment mode when the substrate is in an unworn state, wherein, during the phototherapy treatment mode, the control module directs the UV-B light emitting source to deliver a predetermined amount of UV-B radiation into the body part of the patient, the control module determining the predetermined amount of ultraviolet radiation as a function of a patient's susceptibility to ultraviolet radiation, wherein, during the cleaning treatment mode, the control module directs the UV-C light emitting source to deliver UV-C radiation to a surface of an object based on user input received and operational data that is not related to skin, and wherein both the reflective outer layer and the reflective side layer reflect ultraviolet radiation generated from the set of ultraviolet light emitting sources towards a light emitting region.

2. The wearable ultraviolet light phototherapy device of claim 1, further comprising a reflecting element located at a first end of the substrate, the reflecting element configured to reflect ultraviolet radiation in the substrate, wherein the set of ultraviolet light emitting sources is located at a second end of the substrate, and the first end is opposite the second end.

3. The wearable ultraviolet light phototherapy device of claim 1, wherein the multi-layered substrate further comprises a diffusive layer and a core layer positioned between the reflective outer layer and the diffusive layer, the core layer coupled to the set of ultraviolet light emitting sources, wherein the core layer light guides the ultraviolet radiation generated from the set of ultraviolet light emitting sources, while the reflective outer layer reflects the ultraviolet radiation towards the diffusive layer for transmission into the body part of the patient.

4. The wearable ultraviolet light phototherapy device of claim 3, core layer comprises an ultraviolet transparent layer.

5. The wearable ultraviolet light phototherapy device of claim 3, wherein the diffusive layer comprises a plurality of ultraviolet transparent protrusions configured to extract the ultraviolet radiation from the core layer into the body part of the patient.

6. The wearable ultraviolet light phototherapy device of claim 3, wherein the diffusive layer comprises a layered arrangement of fluoropolymer films and/or light diffusing elements, wherein the layered arrangement of the diffusive layer forms one or more voids.

7. The wearable ultraviolet light phototherapy device of claim 1, further comprising at least one sensor operatively coupled to the set of ultraviolet light emitting sources and the control module to obtain operational data relating to the irradiation of the body part of the patient, wherein the control module controls the operation of the set of ultraviolet light emitting sources as a function of the operational data.

8. The wearable ultraviolet light phototherapy device of claim 7, wherein the at least one sensor comprises an ambient radiation sensor configured to obtain radiation conditions of an ambient environment surrounding the substrate, wherein the control module determines whether there is a need to irradiate the body part of the patient with ultraviolet radiation generated from the set of ultraviolet light emitting sources as a function of the obtained radiation conditions.

9. The wearable ultraviolet light phototherapy device of claim 7, wherein the at least one sensor comprises a fluorescent sensor configured to detect fluorescence emitted from the body part of the patient after irradiation by the set of ultraviolet light emitting sources, wherein the control module is configured to determine changes in the patient's skin based on the detected fluorescence emitted from the body part.

10. The wearable ultraviolet light phototherapy device of claim 7, wherein the at least one sensor and the control module are configured to monitor the irradiation of the body part of the patient with the set of ultraviolet light emitting sources, the control module adjusting the predetermined amount of ultraviolet radiation directed to the body part as a function of the operational data obtained by the at least one sensor.

11. The wearable ultraviolet light phototherapy device of claim 1, wherein the patient's susceptibility is based on skin pigmentation and skin thickness of the patient, and general patient parameters including: skin dryness, skin temperature, age, weight, gender, race, and existing medical conditions and/or medical history, wherein the control module analyzes information associated with the skin pigmentation, the skin thickness, and the general patient parameters to select: an intensity of radiation with the peak wavelength, a spatial coverage, a spectral power distribution, and a duration, that is suited for administration to the patient based on the patient's susceptibility.

12. A wearable ultraviolet light phototherapy device, comprising:
a housing configured to be worn about a body part of a patient, the housing including an inner wall surface and an outer wall surface, wherein the inner wall surface faces a portion of skin of the patient when the housing is worn about the body part and the outer wall surface faces an ambient environment external to the housing;
an input component on the outer wall surface of the housing for receiving information relating to a plurality of general patient parameters and operating parameters;
a set of ultraviolet light emitting sources placed in the housing to direct ultraviolet radiation toward the inner wall surface of the housing for transmission towards the portion of skin of the patient in a phototherapy treatment mode and towards a surface of an object when the housing is in an unworn state in a cleaning treatment mode, wherein at least one of the ultraviolet light emitting sources is an ultraviolet-B (UV-B) light emitting source that operates with a peak wavelength ranging from 295 nm to 315 nm during the phototherapy treatment mode, wherein at least one of the ultraviolet light emitting sources is an ultraviolet-C (UV-C) light emitting source that directs UV-C radiation having a peak wavelength ranging from 100 nm to 280 nm during the cleaning treatment mode, the UV-C light emitting source configured to direct the UV-C radiation toward the inner wall surface of the housing for transmission towards the surface of the object only when the housing is in the unworn state in the cleaning treatment mode for disinfection of the object;

at least one sensor to obtain operational data relating to the irradiation of the portion of skin of the patient during the phototherapy treatment mode and operational data relating to the disinfection of the surface of the object during the cleaning treatment mode, wherein the operational data relating to the disinfection of the surface of the object during the cleaning treatment mode does not include data relating to skin; and a control module operatively coupled to the input component, the set of ultraviolet light emitting sources and the least one sensor to control the irradiation of the portion of skin of the patient during the phototherapy treatment mode and to control the disinfection of the surface of the object during the cleaning treatment mode, wherein, during the phototherapy treatment mode, the control module is configured to:

determine an amount of UV-B radiation to be directed towards the portion of skin of the patient based on the general patient parameters received by the input component and the operational data obtained by the at least one sensor, specify a plurality of irradiation parameters that enable only the UV-B light emitting source to deliver the determined amount of ultraviolet radiation towards the portion of skin of the patient, monitor, using the at least one sensor, the irradiation of the portion of skin of the patient, and adjust one or more of the plurality of irradiation parameters based on feedback provided by the at least one sensor, and wherein, during the cleaning treatment mode, the control module is configured to direct only the UV-C light emitting source to deliver the UV-C radiation to the surface of the object based on user input received by the input component and the operational data that is not related to skin.

13. The wearable ultraviolet light phototherapy device of claim 12, wherein the outer wall surface of the housing comprises an ultraviolet impenetrable material that prevents any ultraviolet radiation generated from the set of ultraviolet light emitting sources from leaking out of the housing into the ambient environment.

14. The wearable ultraviolet light phototherapy device of claim 12, further comprising an infrared camera configured to obtain an infrared image of the patient's skin about the body part of the patient, wherein the control module infers the skin temperature about the body part of the patient from the infrared image, the control module determining the amount of ultraviolet radiation to be directed towards the portion of skin of the patient during the phototherapy treatment mode as a function of the infrared image.

15. The wearable ultraviolet light phototherapy device of claim 12, further comprising a visible camera configured to obtain an image of the patient's skin about the body part of the patient, wherein the visible camera sends the image to the control module for ascertaining the pigmentation and skin thickness about the body part of the patient during the phototherapy treatment mode.

16. The wearable ultraviolet light phototherapy device of claim 12, further comprising at least one visible light emitting source located about the housing to deliver visible light radiation into the portion of skin of the patient during the phototherapy treatment mode.

17. The wearable ultraviolet light phototherapy device of claim 12, wherein the inner wall surface of the housing comprises a light guiding layer that directs the ultraviolet radiation emitted from the set of ultraviolet light emitting sources towards the portion of skin of the patient during the phototherapy treatment mode.

18. The wearable ultraviolet light phototherapy device of claim 12, wherein the inner wall surface of the housing comprises a diffusive layer that directs the ultraviolet radiation emitted from the set of ultraviolet light emitting sources towards the portion of skin of the patient during the phototherapy treatment mode.

19. A wearable ultraviolet light phototherapy system, comprising:

a housing configured to be removably worn about a body part of a patient, the housing including an inner wall surface and an outer wall surface, wherein the inner wall surface faces a portion of skin of the patient while worn and the outer wall surface faces an ambient environment external to the housing;

an input component on the outer wall surface of the housing for receiving information relating to a plurality of general patient parameters and operating parameters;

a camera placed in the housing to obtain an image of the patient's skin about the body part of the patient;

a set of ultraviolet light emitting sources placed in the housing to direct ultraviolet radiation toward the inner wall surface of the housing for transmission towards the portion of skin of the patient in a phototherapy treatment mode and towards a surface of an object when the housing is in an unworn state in a cleaning treatment mode, wherein at least one of the ultraviolet light emitting sources includes an ultraviolet-B (UV-B) light emitting source that operates with a peak wavelength ranging from 295 nm to 315 nm during the phototherapy treatment mode, wherein at least one of the ultraviolet light emitting sources is an ultraviolet-C (UV-C) light emitting source that directs UV-C radiation having a peak wavelength ranging from 100 nm to 280 nm during the cleaning treatment mode, the UV-C light emitting source configured to direct the UV-C radiation toward the inner wall surface of the housing for transmission towards a surface of an object in a cleaning treatment mode for disinfection of the object when the housing is in an unworn state;

at least one sensor to obtain operational data relating to the irradiation of the portion of skin of the patient during the phototherapy treatment mode and operational data relating to the disinfection of the surface of the object during the cleaning treatment mode, wherein the operational data relating to the disinfection of the surface of the object during the cleaning treatment mode does not include data relating to skin; and a control module operatively coupled to the input component, the visible camera, the set of ultraviolet light emitting sources and the least one sensor to control the irradiation of the portion of skin of the patient during the phototherapy treatment mode and to control the disinfection of the surface of the object during the cleaning treatment mode, wherein, during the phototherapy treatment mode, the control module is configured to:

determine an amount of UV-B radiation to be directed towards the portion of skin of the patient based on the general patient parameters received by the input component, the image from the camera, and the operational data obtained by the at least one sensor, specify a plurality of irradiation parameters that enable only the UV-B light emitting source to deliver the determined amount of ultraviolet radiation towards the portion of skin of the patient, monitor, using the at least one sensor and the camera, the irradiation of the portion of skin of the patient, and adjust one or more of the plurality of irradiation parameters based on feedback provided by the at least one sensor and the camera, and wherein, when the housing is in the unworn state, during the cleaning treatment mode, the control module is configured to direct only the UV-C light emitting source to deliver the UV-C radiation to the surface of the object based on user input received by the input component and adjust one or more of the plurality of irradiation parameters based on feedback provided by the at least one sensor including the operational data that is not related to skin.

20. The wearable ultraviolet light phototherapy device of claim 19, wherein the operational data relating to the irradiation of the portion of skin of the patient during the phototherapy treatment mode includes a patient's susceptibility to ultraviolet radiation, which is based on skin pigmentation and skin thickness of the patient, and general patient parameters including: skin dryness, skin temperature, age, weight, gender, race, and existing medical conditions and/or medical history, wherein the control module analyzes information associated with the skin pigmentation, the skin thickness, and the general patient parameters to select: an intensity of radiation with the peak wavelength, a spatial coverage, a spectral power distribution, and a duration, that is suited for administration to the patient based on the patient's susceptibility.

\* \* \* \* \*